(12) United States Patent
Turdiev

(10) Patent No.: US 9,120,843 B2
(45) Date of Patent: Sep. 1, 2015

(54) AGENT DERIVED FROM TORTOISE SPLEEN STIMULATING MAMMALIAN HEMOPOIESIS

(71) Applicant: BMR Solutions Ltd., Herzlia (IL)

(72) Inventor: Azim Turdiev, Caesarea (IL)

(73) Assignee: BMR Solutions Ltd., Herzlia (IL)

(*) Notice: Subject to any disclaimer, the term of this patent is extended or adjusted under 35 U.S.C. 154(b) by 0 days.

(21) Appl. No.: 14/455,973

(22) Filed: Aug. 11, 2014

(65) Prior Publication Data

US 2014/0348804 A1 Nov. 27, 2014

Related U.S. Application Data

(60) Division of application No. 13/681,552, filed on Nov. 20, 2012, now Pat. No. 8,802,817, which is a continuation of application No. 13/195,093, filed on Aug. 1, 2011, now Pat. No. 8,329,864, which is a continuation of application No. 10/570,456, filed as application No. PCT/IL2004/000789 on Aug. 31, 2004, now Pat. No. 8,003,756.

(30) Foreign Application Priority Data

Sep. 4, 2003 (IL) .......................................... 157772

(51) Int. Cl.
| | |
|---|---|
| C07K 5/10 | (2006.01) |
| C07K 5/107 | (2006.01) |
| A61K 38/07 | (2006.01) |
| A61K 45/06 | (2006.01) |
| A61K 35/28 | (2015.01) |
| A61K 38/00 | (2006.01) |

(52) U.S. Cl.
CPC .............. *C07K 5/1016* (2013.01); *A61K 35/28* (2013.01); *A61K 38/07* (2013.01); *A61K 45/06* (2013.01); *A61K 38/00* (2013.01)

(58) Field of Classification Search
CPC .............................. C07K 5/1016; A61K 38/07
USPC ........................................... 530/329; 514/7.9
See application file for complete search history.

(56) References Cited

U.S. PATENT DOCUMENTS

| | | | |
|---|---|---|---|
| 5,866,160 A | 2/1999 | Hong et al. | |
| 5,968,513 A | 10/1999 | Gallo et al. | |
| 6,248,587 B1 | 6/2001 | Rodgers et al. | |
| 8,003,756 B2 | 8/2011 | Turdiev | |
| 8,329,864 B2 | 12/2012 | Turdiev | |
| 2002/0127219 A1 | 9/2002 | Okkels et al. | |
| 2003/0007976 A1* | 1/2003 | Watson et al. | 424/184.1 |
| 2003/0134314 A1* | 7/2003 | Carroll et al. | 435/6 |
| 2006/0223077 A1 | 10/2006 | Ni et al. | |
| 2007/0111948 A1 | 5/2007 | Turdiev | |
| 2011/0288271 A1 | 11/2011 | Turdiev | |
| 2013/0129689 A1 | 5/2013 | Turdiev | |

FOREIGN PATENT DOCUMENTS

| | | |
|---|---|---|
| EP | 0377044 | 7/1990 |
| EP | 1018559 | 7/2000 |
| WO | WO 01/049830 | 7/2001 |

OTHER PUBLICATIONS

Office Action Dated Feb. 4, 2014 From the Israel Patent Office Re. Application No. 157772 and Its Translation Into English.
Office Action Dated Jun. 5, 2007 From the Israel Patent Office Re. Application No. 157772.
Office Action Dated Jun. 5, 2012 From the Israel Patent Office Re. Application No. 157772 and Its Translation into English.
Office Action Dated Sep. 16, 2013 From the Israel Patent Office Re. Application No. 157772 and Its Translation Into English.
Office Action Dated Dec. 23, 2014 From the Israel Patent Office Re. Application No. 157772.
Office Action Dated Dec. 25, 2007 From the Israel Patent Office Re. Application No. 157772.
Official Action Dated Jul. 2, 2008 From the US Patent and Trademark Office Re. U.S. Appl. No. 10/570,456.
Official Action Dated Nov. 15, 2013 From the US Patent and Trademark Office Re. U.S. Appl. No. 13/681,552.
Official Action Dated Jan. 20, 2012 From the US Patent and Trademark Office Re. U.S. Appl. No. 13/195,093.
Official Action Dated Jul. 20, 2007 From the US Patent and Trademark Office Re. U.S. Appl. No. 10/570,456.
Official Action Dated Feb. 27, 2008 From the US Patent and Trademark Office Re. U.S. Appl. No. 10/570,456.
Restriction Official Action Dated Dec. 12, 2011 From the US Patent and Trademark Office Re. U.S. Appl. No. 13/195,093.
Restriction Official Action Dated Sep. 20, 2013 From the US Patent and Trademark Office Re. U.S. Appl. No. 13/681,552.
Supplemental Notice of Allowability Dated Nov. 2, 2012 From the US Patent and Trademark Office Re. U.S. Appl. No. 13/195,093.
Translation Dated Jan. 15, 2015 of Office Action Dated Dec. 25, 2007 From the Israel Patent Office Re. Application No. 157772.
Bonnet et al. "Cytokine Treatment or Accessory Cells Are Required to Initiate Engraftment of Purified Primitive Human Hematopoietic Cells Transplanted at Limiting Doses into NOD/SCID Mice", Bone Marrow Transplantation, 23: 203-209, 1999.
Golde "The Stem Cell", Scientific American, 36: 86-93, Dec. 1991.
Gosselin et al. "Amifostine as a Radioprotectant", Clinical Journal of Oncology Nursing, 6(3): 175-177, 2002.
Gurevitch et al. "Osteogenic Growth Peptide Increases Blood and Bone Marrow Cellularity and Enhances Engraftment of Bone Marrow Transplants in Mice", Blood, 88(12): 4719-4724, Dec. 15, 1996. Abstract.

(Continued)

*Primary Examiner* — David Lukton

(57) ABSTRACT

The present invention relates to a proteinaceous extract derived from tortoise spleen and to a tetrapeptide FTGN, which have stimulatory activity on hematopoietic cells. In particular, this tetrapeptide enhances hemopoietic reconstruction, and bone marrow re-population, reduced as a consequence of a high dose of radiation or chemotherapy exposure. The invention further provides pharmaceutical compositions comprising as an effective ingredient the proteinaceous extract or the FTGN tetrapeptide and ex vivo and in vivo methods of treatment employing them.

7 Claims, 17 Drawing Sheets

(56) References Cited

OTHER PUBLICATIONS

Jacobson et al. "The Influence of the Spleen on Hematopoietic Recovery After Irridation Injury", Proceedings of the Society of Experimental Biology and Medicine, 73: 455-459, 1950.

Khamidov et al. "Blood and Haemopoiesis of Vertebrates With Radiation Injuries", Monograph, Tashekent, FAN, p. 175. Abstract in English.

King et al. "Regulation of Colony-Stimulating Activity Production From Bone Marrow Stromal Cells by the Hematoregulatory Peptide, HP-5", Experimental Hematology, 20: 223-228, 1992.

Mauch et al. "Loss of Hematopoietic Stein Cell Self-Renewal After Bone Marrow Transplantation", Blood, 74(2): 872-875, Aug. 1, 1989. Abstract.

Merck "Table of Contents", The Merck Index, An Encyclopedia of Chemicals, Drugs, and Biologicals, 12th Ed., 1996.

Morrison et al. "The Purification and Characterization of Fetal Liver Hematopoietic Stem Cells", Proc. Natl. Acad. Sci. USA, 92: 10302-10306, 1995.

Pelus et al. "In Vivo Modulation of Hematopoiesis by a Novel Hematoregulatory Peptide", Experimental Hematology, 22: 239-247, 1994.

Rafii et al. "Human Bone Marrow Microvascular Endothelial Cells Support Long-Term Proliferation and Differentiation of Myeloid and Megakaryocytic Progenitors", Blood, 86(9): 3353-3363, Nov. 1, 1995. Abstract.

Soederdahl et al. "Cadaveric Bone Marrow and Spleen Cells for Transplantation", Bone Marrow Transplantation, 21(1): 79-84, Jan. 1998. Abstract.

Thorsteinsdottir et al. "Enhanced In Vivo Regenerative Potential of HOXB4-Transduced Hematopoietic Stem Cells With Regulation of Their Pool Seize", Blood, 94(8): 2605-2612, Oct. 15, 1999. Abstract.

Tudiyev et al. "The Influence of U-2 Fraction of a Tortoise Spleen Extract on the Formation of Ectopic Locus of Haemopoiesis", Radiobiology, 30(5): 699-701, 1990. Abstract in English.

Turdiev et al. "Stimulation of the the Bone Marrow Stem Cells by Tortoise Spleen Extract", In Vivo Biological/Clinical Use of Growth Factors and Cykines, Excluding Stem Cell Collection, XP008043807, 96(11-12): 156B-157B, # 4381, 2000.

Turdyev et al. "Postirradiation Recovery of the Haemopoietic Function of Mice Treated With Acelluar Components of T. Horsfieldi Tissues", Radiobiology, 25: 655, 1985. Abstract in English.

Turdyev et al. "The Therapeutic Effect of Purified Compounds of a Tortoise Spleen Extract", Radiobiology, XP008043777, 26(5): 685-688, 1985. Abstract in English.

Turdyiev et al. "Radiotherapeutic and Immunostimulating Effect of 'Tortezin' Compound From Central Asian Toroise", Radiation Biology and Radioecology, 38: 207-214, 1998. Abstract in English.

Vellenga et al. "Different Repopulation Kinetics of Erythroid (BFU-E), Myeloid (CFU-GM) and T Lymphocyte (TL_CFU) Progenitor Cells After Autologous and Allogeneic Bone Marrow Transplantation", British Journal of Haematology, 65: 137-142, 1987.

Watson et al. "Novel Factors From Stromal Cells: Bone Marrow and Thymus Microenvironments", International Journal of Cell Cloning 10: 144-152, 1992.

\* cited by examiner

SEQUENCE LISTING

<160> NUMBER OF SEQ ID NOS: 1

<210> SEQ ID NO 1
<211> LENGTH: 4
<212> TYPE: PRT
<213> ORGANISM: Testudo horsfieldi

<400> SEQUENCE: 1

Phe Thr Gly Asn
1

AGENT DERIVED FROM TORTOISE SPLEEN STIMULATING MAMMALIAN HEMOPOIESIS

RELATED APPLICATIONS

This application is a division of U.S. patent application Ser. No. 13/681,552 filed on Nov. 20, 2012, now U.S. Pat. No. 8,802,817 which is a continuation of U.S. patent application Ser. No. 13/195,093 filed on Aug. 1, 2011, now U.S. Pat. No. 8,329,864, which is a continuation of U.S. patent application Ser. No. 10/570,456 filed on Oct. 24, 2006, now U.S. Pat. No. 8,003,756, which is a National Phase of PCT Patent Application No. PCT/IL2004/000789 filed on Aug. 31, 2004, which claims the benefit of priority of Israel Patent Application No. 157772 filed on Sep. 4, 2003. The contents of all of the above applications are incorporated by reference as if fully set forth herein.

SEQUENCE LISTING STATEMENT

The ASCII file, entitled 60136SequenceListing.txt, created on Aug. 10, 2014, comprising 4,096 bytes, submitted concurrently with the filing of this application is incorporated herein by reference.

FIELD OF THE INVENTION

The present invention relates to a proteinaceous agent derived from tortoise spleen, and to an oligopeptide that stimulates the proliferation of mammalian hemopoietic cells. More specifically, these compounds enhance engraftment of bone marrow transplant, hemopoietic reconstruction and bone marrow re-population and therefore can be used for curing and/or alleviating the detrimental effect of ionizing radiation and/or cytotoxic chemicals on a tissue or body. The invention further provides methods for using this tetrapeptide and pharmaceutical compositions comprising it.

BACKGROUND OF THE INVENTION

Exposure to ionizing radiation has detrimental effects on tissues; and exposure of hemopoietic cells to such radiation, may provoke life threatening consequences. Radiation therapy is an important regimen of many anticancer treatments, together with chemotherapy, where cytotoxic effects of both these therapies often affect hemopoiesis. Therefore, protecting agents could substantially improve the efficiency of current anticancer therapies, in addition to their possible use in cases of accidental irradiation. Radiotherapy is a treatment for cancer and other diseases that incorporates ionizing radiation to destroy malignancies. Ionizing radiation damages or destroys cells in the area being treated, preventing the malignant cells from continuing to grow and multiply. Most radiotherapy techniques employ high energy X-rays or sometimes Gamma rays. In some instances internal radiotherapy (e.g. radioactive implant placed inside the body) may be used.

Radiotherapy can damage normal cells as well as cancer cells, and there may be potential side effects, which would depend on the radiotherapy dose, site(s) of treatment, age and other factors. The side effects of radiation therapy include temporary or permanent loss of hair in the area being treated, skin irritation, temporary change in skin color in the treated area, and tiredness.

Since radiation therapy can be and often is used in combination with chemotherapy or surgery, other common side effects as fatigue, pain, nausea, vomiting, decreased blood cell counts, hair loss, and mouth sores may worsen the patient's condition and also increase the patient's discomfort.

One of currently used protections against radiation damages is the transplantation of bone marrow or administration of peripheral blood stem cells in early days post irradiation or chemotherapy. However, the hematopoietic stem cells recover to only 5% to 10% of normal levels after bone marrow transplantation [Mauch P. et al.: Blood (1989) Vol. 74(2):972; Thorsteinsdottir U. et al.: Blood (1999) Vol. 94 (8):2605], and recovery time is too long [Vellenga E. et al.: British J. Haematol. (1987) Vol. 65(2):137], not mentioning the problems of bone marrow storage [Soderdahl G. et al.: Bone Marrow Transplant (1998) Vol. 21(1):79].

The ability to modulate differentiation and proliferation of hematological precursors is at the basis of the more innovative therapies such as peripheral blood stem cell transplant, gene transfection and ex vivo expansion of stem cells. In spite of this impressive progress, several aspects of stem cell physiology have not been fully clarified.

Several factors are suspected of being involved in the physiological or pathological proliferation/differentiation of bone marrow cells. In addition to the role of classically defined growth factors, several biological agents and cell types could improve or modify both in vivo and ex vivo therapeutic strategies. Human bone marrow-derived endothelial cells support long term proliferation and differentiation of myeloid and megakaryocytic progenitors [Rafii, S., et al., Blood (1995) Vol. 86:353]; accessory cells may support hematological recovery after bone marrow transplant [Bonnet, D., et al., Bone Marrow Transpl. (1991) Vol. 23:203].

Short peptides have been synthesized to reach hemoregulatory and multilineage effects, possibly by enhancement of cytokine production by stromal cells [King, A. G., et al., Exp. Hematol. (1992) Vol. 20(4):531; Pelus, L. M., et al., Exp. Hematol. (1994) Vol. 22:239].

For example, the osteogenic growth peptide (OGP) was shown to induce, in vivo, a balanced increase in white blood cell (WBC) counts, and overall bone marrow cellularity in mice receiving myeloablative irradiation and syngeneic or semiallogeneic bone marrow transplants [Gurevitch, O., et al., Blood (1996) Vol. 88(12):4719].

Therefore, substances that can induce increment in colony forming units (CFU) capacity of bone marrow cells and related cells along the different differentiation paths, should find clinical application in treatments intending to restore the hematopoietic cells damaged by chemotherapeutic agents and/or radiation.

Oligopeptides that support hemopoiesis may prove useful in other ways as well. Some investigators have found that adding stem cells from peripheral blood to those from bone marrow significantly increases the rate of engraftment. However, extracting sufficient numbers of stem cells from peripheral blood is a complicated procedure. Administering such oligopeptides to donors to increase the number of stem cells in the blood will improve the feasibility of transplanting stem cells from peripheral blood [Golde, D. W., Sci. Am. (1991) Vol. 36 (December)].

The capacity of the hematopoietic stem cells to provide for the lifelong production of all blood lineages is accomplished by a balance between the plasticity of the stem cell, that is the production of committed progenitor cells which generate specific blood lineages, and the replication of stem cell in the undifferentiated state (self-renewal). The mechanisms regulating hematopoietic stem cells plasticity and self-renewal in vivo have been difficult to define. However, the major contributory factors represent a combination of cell intrinsic and environmental influences [Morrison, et al., Proc. Natl. Acad. Sci. USA (1995) Vol. 92:10302].

A prerequisite for hemopoiesis and therefore successful BMT is the presence of functional stromal cells and tissue that form part of the hemopoietic microenvironment, determine the homing of the injected stem cells from the circulation to the bone marrow and support hemopoiesis [Watson, J. D. and McKenna, H. J. Int. J. Cell Cloning (1992) Vol. 10:144]. Growth of bone marrow cells is supported by the stromal tissue. The tissue components provide the conditions needed for the survival of stem cells in long-term in vitro bone marrow cultures. At present this technology suffices to keep stem cells alive. Adding an appropriate factor, e.g. a "hemopoietic" oligopeptide to these cultures may help expand the stem cell population ex vivo/in vitro, thus providing increased numbers of these cells for transplantation.

A combined in vitro/in-vivo approach may provide the basis for a forward-looking strategy for (i) obtaining small stem cell preparations from donors of blood or marrow and (ii) enabling healthy individuals to have their stem cells stored for any future therapeutic need, thus bypassing the complexity associated with the use of allogeneic BMT.

It would therefore be of therapeutic importance to use small peptides such as the oligopeptide described in the present application, that stimulate post-BMT hemopoietic reconstruction by enhancing in vivo, ex vivo and/or in vitro the progenitor hemopoietic cells.

A largely used protective agent is amifostine [Merck Index, 12th Ed.], a thiophosphate developed by the US army as a radioprotective agent, and currently used to decrease the cytotoxic effects of both radiation therapy and chemotherapy. Amifostine must be administered shortly before irradiation; once reconstituted, its stability at room temperature is quite limited [Gosselin T. K. and Mautner B.: Clin. J. Oncology Nursing (2002) Vol. 6:175]. Most patients are afflicted by some of many side effects of amifostine, which include, e.g., hypotension, allergies, nausea and vomiting, the latter two occurring in approximately 53% of patients [Gosslin and Mautner, Ibid.].

The development of a non-toxic selective protective agent that preferentially protects normal tissues from chemotherapy toxicity, without protecting malignant tissues, is a major challenge in cancer chemotherapy research. The available protective agents are either toxic or lack selective protective activity.

It is therefore an object of this invention to provide a new protective agent, conferring protection to a tissue or body exposed to a cytotoxic factor, such as ionizing irradiation or cytotoxic chemical.

The tortoise is a quite remarkable animal in that it can survive a dose of ionizing radiation greater than other vertebrata, and nearly 100-times greater than mammals (Table 1) [Khamidov D. K. et al.: Blood and Haemopoiesis of Vertebrates with Radiation Injuries, Monograph, Tashkent (1986), "FAN" 175 pp.].

TABLE 1

Lethal doses of ionizing radiation for different animals

| Animal | Lethal dose - $LD_{50/30}$ (Gy) |
| --- | --- |
| Golden fish | 25 |
| Frog | 15 |
| Lizard | 25 |
| Tortoise | 500 |
| Pigeon | 15 |
| Mouse | 7 |

EP 0377044 B1 describes a protective effect of a nonapeptide (EAKSQGGSN) on irradiated mice. U.S. Pat. No. 5,866,160 describes a composition of soft-shelled turtle and tortoise, for enhancing the leukocyte number in patients undergoing chemotherapy. Russian Patent RU 2118533C1 describes an extract from tortoise liver for improving hematopoietic function in irradiated mammals, and for increasing their viability. Jacobson [Jacobson L. O. et al.: Proc. Soc. Exptl. Biol. Med. (1950) Vol. 73:455] demonstrated an important role of spleen by screening the said organ during irradiation of mice, and finding that their survival rate significantly increased.

It was found that intraperitoneal injection of tortoise plasma increased the survival rate of mice after whole body γ-irradiation (8 Gray; Gy) and that the injection of a spleen extract had a still stronger effect [Turdiev A. et al.: Radiobiology (1985) Vol. 25:655; Turdiev A. et al.: Radiation Biology and Radioecology (1998) Vol. 38:63].

It is therefore another object of this invention to provide a new protective agent conferring protection to a tissue or body exposed to a cytotoxic factor, such as an ionizing irradiation or a cytotoxic chemical, wherein said protective agent is derived from tortoise spleen.

It is further an object of this invention to provide a pharmaceutical composition comprising a factor or oligopeptide derived from tortoise spleen, that can decrease damages caused by an ionizing irradiation to a tissue or body, wherein said irradiation is either accidental or a part of radiation therapy.

It is a still further object of this invention to provide a pharmaceutical composition comprising a factor or oligopeptide derived from tortoise spleen that can decrease damages caused to a tissue or body by an exposure to a cytotoxic chemical, wherein said exposure is either accidental or a part of chemotherapy.

Other objects and advantages of present invention will become apparent as description proceeds.

SUMMARY OF THE INVENTION

The present invention relates to a proteinaceous composition of matter derived from tortoise spleen capable of stimulating the proliferation of mammalian hemopoietic cells.

In a preferred embodiment, the composition of matter of the invention comprises an oligopeptide having molecular weight up to 2000 Daltons, preferably an oligopeptide that comprises from 4 to 20 amino acids, and particularly an oligopeptide comprising the amino acid sequence FTGN (SEQ ID: No. 1).

The composition of matter of the invention stimulates the proliferation of mammalian hemopoietic cells, enhances hemopoiesis in an irradiated subject, increases spleen mass, increases bone marrow count, and/or improves the probability of survival of said irradiated subject. More particularly, the composition of matter of the invention increases bone marrow cells (BMC) count in an irradiated subject following transplantation of bone marrow cells which have been exposed to said composition of matter before being transplanted into said irradiated subject.

The invention further relates to an oligopeptide comprising the amino acid sequence FTGN (SEQ ID: No. 1), preferably an oligopeptide having the amino acid sequence FTGN (SEQ ID: No. 1) or its biologically functional variants, modifications and derivatives, its physiologically acceptable salts, esters and amides of said oligopeptide and derivatives thereof that maintain the ability to stimulate the proliferation of mammalian hemopoietic cells, In a further aspect the invention relates to biologically functional variants of the oligopeptide of the invention, wherein such variant may comprise an alteration in the side chain of an amino acid of said oligopeptide, resulting from either in vivo mutation or from chemical modification in vitro; a dimer or multimer of said oligopeptide.

The invention also relates to the oligopeptide modifications wherein said modification or derivative comprises a chemical modification of side chains of the amino acids, or modification of the terminal carboxyl or amino groups, alkylation, acylation, amidation, or esterification, in which said modification modulates the biological activity of said oligopeptide, and/or improves its stability in vivo.

In a special embodiment, the invention relates to a protective composition for in vivo treatment, preferably by injection, comprising an oligopeptide or physiologically acceptable salts, esters, and amides of said oligopeptide or its variants, modifications, and derivatives, for reducing the detrimental effect of a cytotoxic factor selected from ionizing radiation and cytotoxic chemicals on a tissue or body exposed thereto, wherein the exposure of tissue or body to ionizing radiation or cytotoxic chemical is accidental or a part of radiation therapy or chemotherapy. Said composition being useful for in vitro or ex vivo treatment of hemopoietic cells.

In another aspect, the invention describes a pharmaceutical composition comprising an oligopeptide as active ingredient, preferably a tetrapeptide having the amino acid sequence FTGN (SEQ ID: No. 1), its physiologically acceptable salts, esters, and amides of said oligopeptide or its functional variants, modifications, and derivatives further comprising pharmaceutically acceptable carriers, excipients and/or diluents. Said pharmaceutical composition may further comprise an additional active agent selected from growth factors, anti-rejection agents or tolerance inducing agents, analgesics, antibiotics, anti-inflammatory agents, antineoplastics, cyto-protectants, glucocorticoids, hematopoietics, and immunosuppressants.

In a preferred embodiment, the invention relates to a method for reducing the detrimental effect of a cytotoxic factor selected from ionizing radiation and cytotoxic chemicals on a mammalian subject exposed thereto, comprising administering to said subject a composition of matter or an oligopeptide or a physiologically acceptable salt, ester, or amide thereof or a variant, modification, or derivative thereof. This method comprises the steps of: obtaining hemopoietic cells of said mammal; ex vivo treatment of said hemopoietic cells with the composition of matter of the invention, or with an oligopeptide according to the invention or with physiologically acceptable salts, esters, and amides thereof or with functional variants, modifications, and derivatives thereof as previously defined; and re-implanting said cells into said mammal wherein treated cells are donor's hemopoietic cells.

In a different embodiment, the method of the invention may be applied for reducing the detrimental effect of a cytotoxic factor selected from ionizing radiation and cytotoxic chemicals on a tissue or body of a mammalian subject exposed to said factor, wherein the exposure of said tissue or subject to ionizing radiation or cytotoxic chemical/factor is accidental or a part of a radiation/chemotherapy, by directly administering to said mammal a composition of matter, or an oligopeptide or physiologically acceptable salts, esters, and amides thereof or functional variants, modifications, and derivatives thereof as defined above.

In a preventive approach, the method of the invention may comprise an initial step wherein cells are treated with said composition of matter or said peptide or said derivative before the exposure to said cytotoxic factor.

The invention also relates to the use of the composition of matter, or oligopeptide, or physiologically acceptable salts, esters, and amides thereof or variants, modifications, and derivatives thereof, all according to the invention, in the preparation of a medicament for reducing the detrimental effect of a cytotoxic factor selected from ionizing radiation and cytotoxic chemicals on a tissue or body of a mammal exposed thereto.

In a more specific embodiment, the invention relates to the use of a tetrapeptide having the amino acid sequence FTGN (SEQ ID: No. 1), a pharmaceutically acceptable salt thereof, or a functional derivate thereof obtained by esterification, amidation, alkylation, or acylation, in the preparation of a medicament.

The invention thus encompasses a composition of matter, an oligopeptide or physiologically acceptable salts, esters, and amides thereof or functional variants, modifications, and derivatives thereof, for use as a medicament for reducing the detrimental effect of a cytotoxic factor selected from ionizing radiation and cytotoxic chemicals on a tissue or body of a mammal exposed thereto.

More specifically, the active factor of said medicament is a tetrapeptide having the amino acid sequence FTGN (SEQ ID: No. 1), or pharmaceutically acceptable salts or physiologically acceptable functional derivatives thereof comprising alkylation, acylation, amidation, or esterification, of said tetrapeptide.

In another embodiment, the invention relates to an oligopeptide comprising the amino acid sequence FTGN (SEQ ID: No. 1), preferably a tetrapeptide having the amino acid sequence FTGN (SEQ ID: No. 1) or physiologically acceptable salts, esters, and amides thereof, or its variants, modifications, and derivatives maintaining the capability to stimulate the proliferation of mammalian hemopoietic cells, for use as a cyto-protective agent.

The above and other characteristics and advantages of the invention will be more readily apparent through the following examples, and with reference to the appended drawings, wherein:

Different separated fractions were obtained after HPLC: fractions a-h.

Abbreviations: Fract.: fraction; T: time; Min: minutes.

Figure 2:
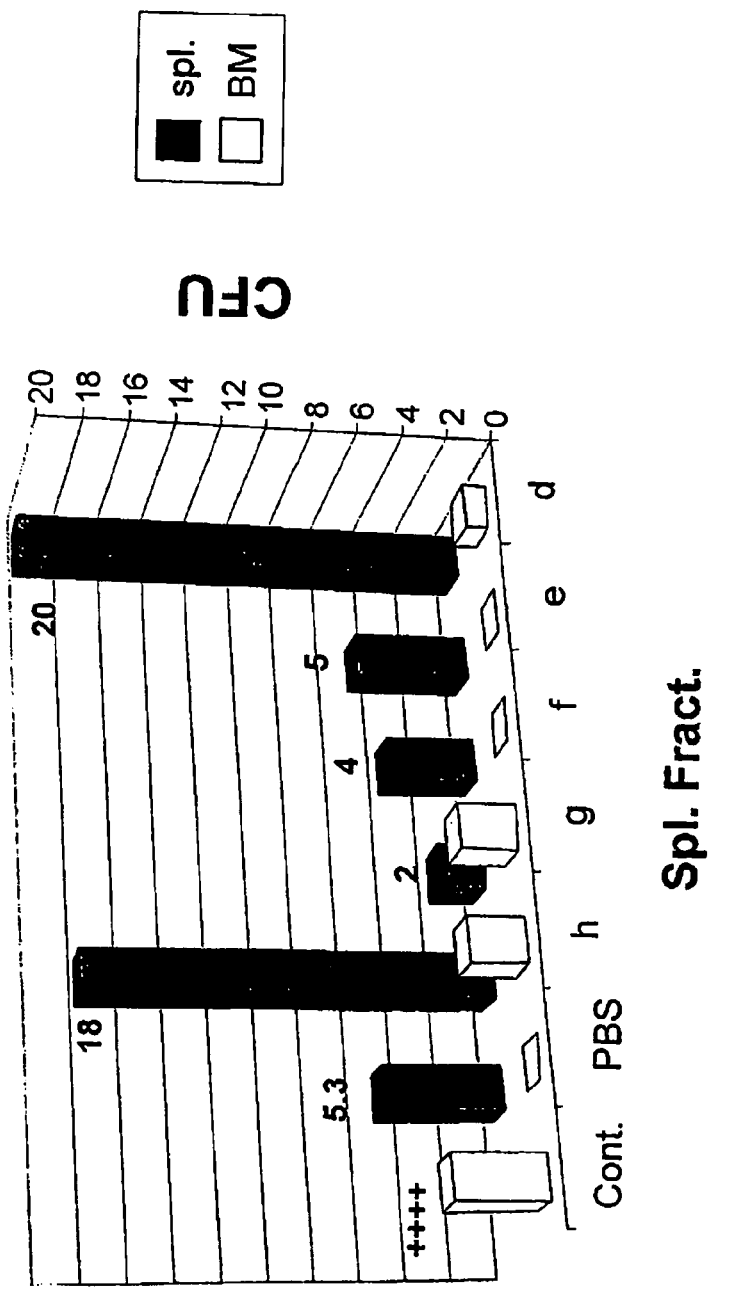

FIG. 2: Biological activity of the different tortoise spleen extracts HPLC fractions Irradiated mice (6Gy) were injected with 2 μg of the purified fractions d-h. The hemopoietic activity in the mice was evaluated at the $14^{th}$ day post-irradiation by assessing the number of colonies originated from spleen and bone marrow cells. The fraction treatment results are compared to control mice (irradiated but not treated) or PBS mice (irradiated and injected with PBS buffer).

Abbreviations: Spl. Fract.: spleen fraction; Sp.: spleen; BM: bone marrow; CFU: colony forming units; Cont.: control.

FIG. 3a-d: Biological activity of the tortoise spleen extract HPLC fraction a.

Bone marrow cells were treated ex vivo with fraction a or PBS and transplanted into irradiated mice.

Figure 3A:

FIG. 3a: Bone marrow smear of an irradiated mouse without any treatment.

Figure 3B:
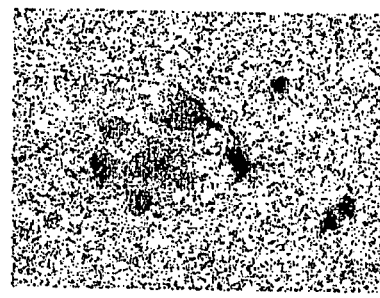

FIG. 3b: Bone marrow smear of an irradiated mouse transplanted with BMC treated with PBS.

Figure 3C:
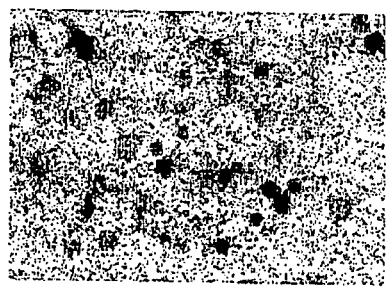

FIG. 3c: Bone marrow smear of an irradiated mouse transplanted with BMC treated with the spleen extract fraction a.

Figure 3D:

FIG. 3d: Spleen morphology of the mice from FIGS. 3a-3c as seen at the ninth day after irradiation. Left: control mice, Middle: mice transplanted with BMC treated with PBS, Right: mice transplanted with BMC previously treated with fraction a.

Figure 4:
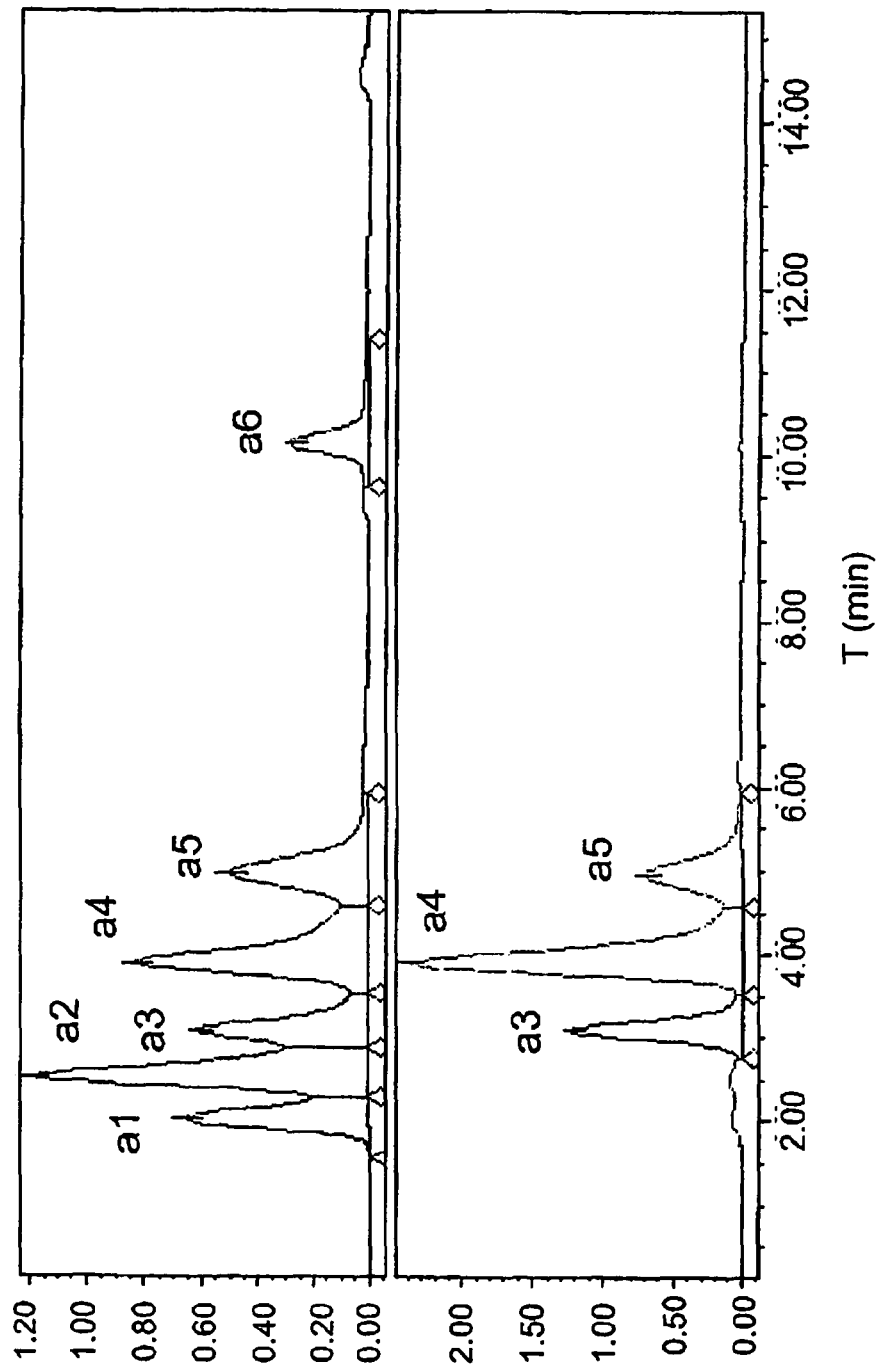

FIG. 4: HPLC chromatogram sub fractionation of fraction a.

Active spleen extract fraction a was further purified to sub-fractions a1-a6.

Abbreviations: T: time; Min: minutes.

Figure 5:
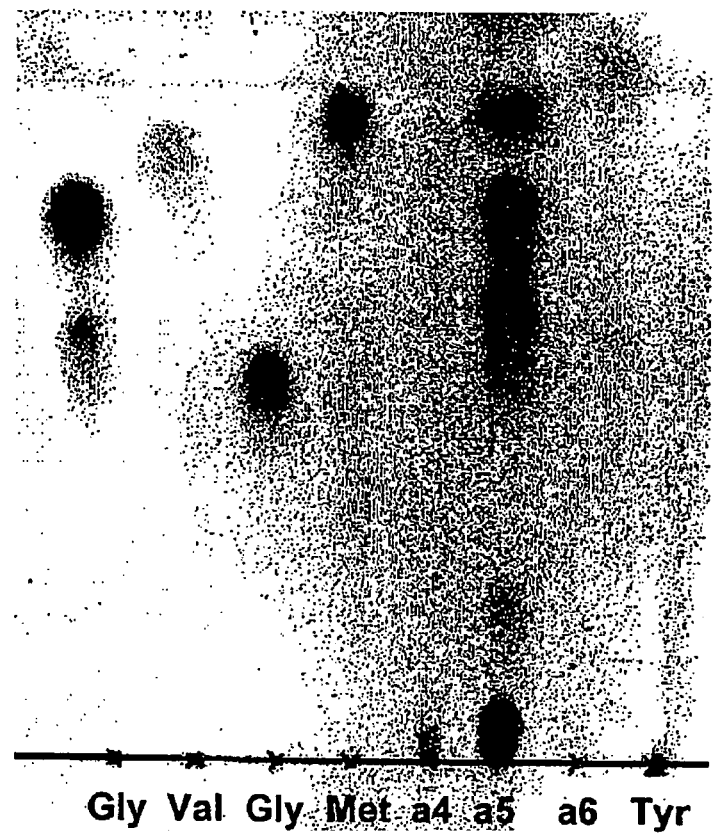

FIG. 5: TLC chromatogram comprising fractions a4 to a6.

Thin layer chromatography of sub-fractions a4, a5 and a6. Fraction a5 shows the presence of oligopeptides. Control amino acids Glu, Val, Gly, Met and Tyr were included.

Figure 6A:
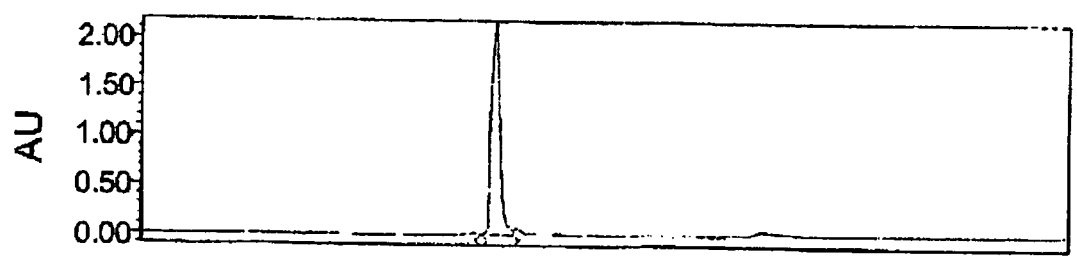
Figure 6B:
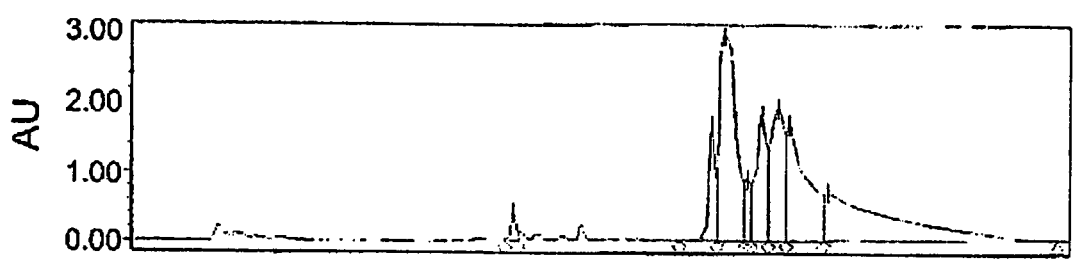
Figure 6C:
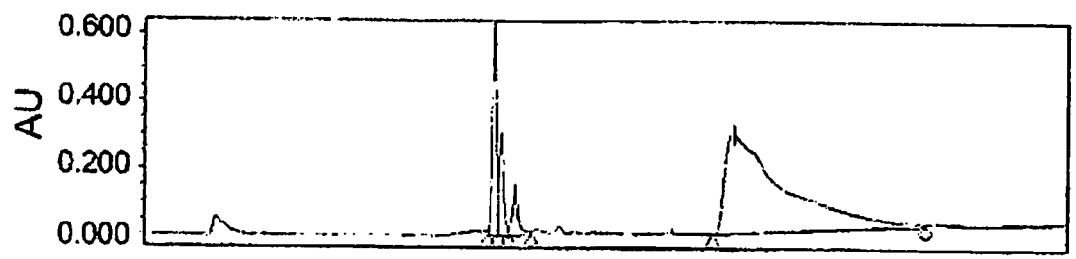

FIG. 6a-c: FTGN tetrapeptide stability.

FIG. 6a: HPLC chromatogram of FTGN tetrapeptide reconstituted in water after storage at −100° C. for one year.

FIG. 6b: HPLC chromatogram of normal blood serum

FIG. 6c: HPLC chromatogram of FTGN tetrapeptide reconstituted in serum and incubated at 37° C. during 4 hours.

Abbreviations: T: time; Min: minutes; AU: arbitrary units.

Figure 7:
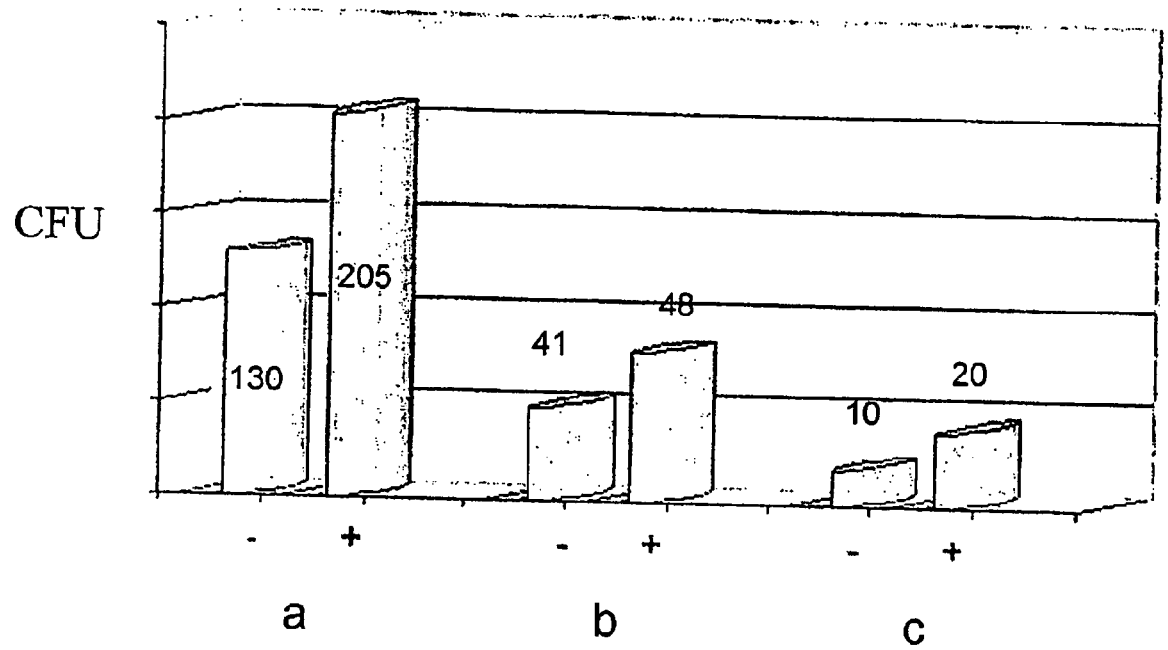

FIG. 7a-c: FTGN tetrapeptide biological activity tested in vitro.

BM cells were incubated in vitro in RPMI medium in the presence (10 µg/ml) or absence of FTGN tetrapeptide for 2 hours. Cells were washed and cloned in methylcellulose-containing medium.

FIG. 7a: BM cells from non irradiated mice incubated in the presence (+) or absence (−) of FTGN tetrapeptide.

FIG. 7b: BM cells from irradiated mice (4.5 Gy) 24 hours previous to the incubation in the presence (+) or absence (−) of FTGN tetrapeptide.

FIG. 7c: BM cells from non irradiated mice, irradiated ex vivo (4.5 Gy) and incubated in the presence (+) or absence (−) of FTGN tetrapeptide.

Abbreviations: CFU: colony forming units.

Figures 8A, 8B:

FIG. 8a-b: Spleen morphology of irradiated mice transplanted with BMC pre-treated with FTGN.

Total body irradiated mice (7.0 Gy) were injected with $6\times10^4$ BMC previously treated with FTGN tetrapeptide.

FIG. 8a: Spleens from mice transplanted with FTGN treated BMC, 4, 9 and 16 days after transplant.

FIG. 8b: Spleens from mice transplanted with untreated BMC, 4, 9 and 16 days after transplant Abbreviations: T: time; D: days.

Figure 9:
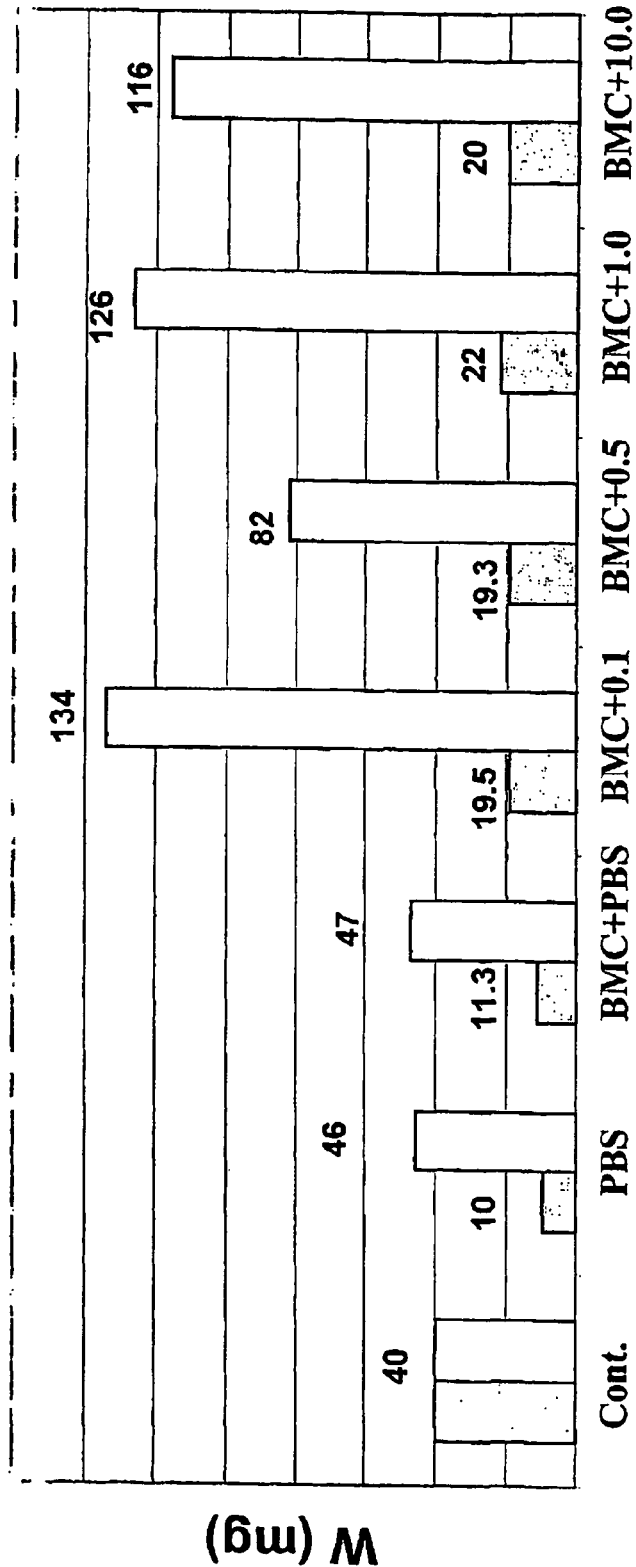

FIG. 9: Spleen weight of irradiated mice transplanted with BMC pre-treated with FTGN.

Total body irradiated mice (7.5 Gy) were injected with $6\times10^4$ BMC previously treated with FTGN tetrapeptide at different concentrations (0.1, 0.5, 1.0 and 10.0 µg/ml). Spleen weight was measured 9 (dark columns) and 16 (clear columns) days after irradiation and compared to control mice (normal non-irradiated mice) or PBS mice (mice transplanted with BMC incubated with PBS).

Abbreviations: Treat.: treatment; BMC: bone marrow cells; W: weight; mg: milligrams; Cont.: control.

Figure 10:
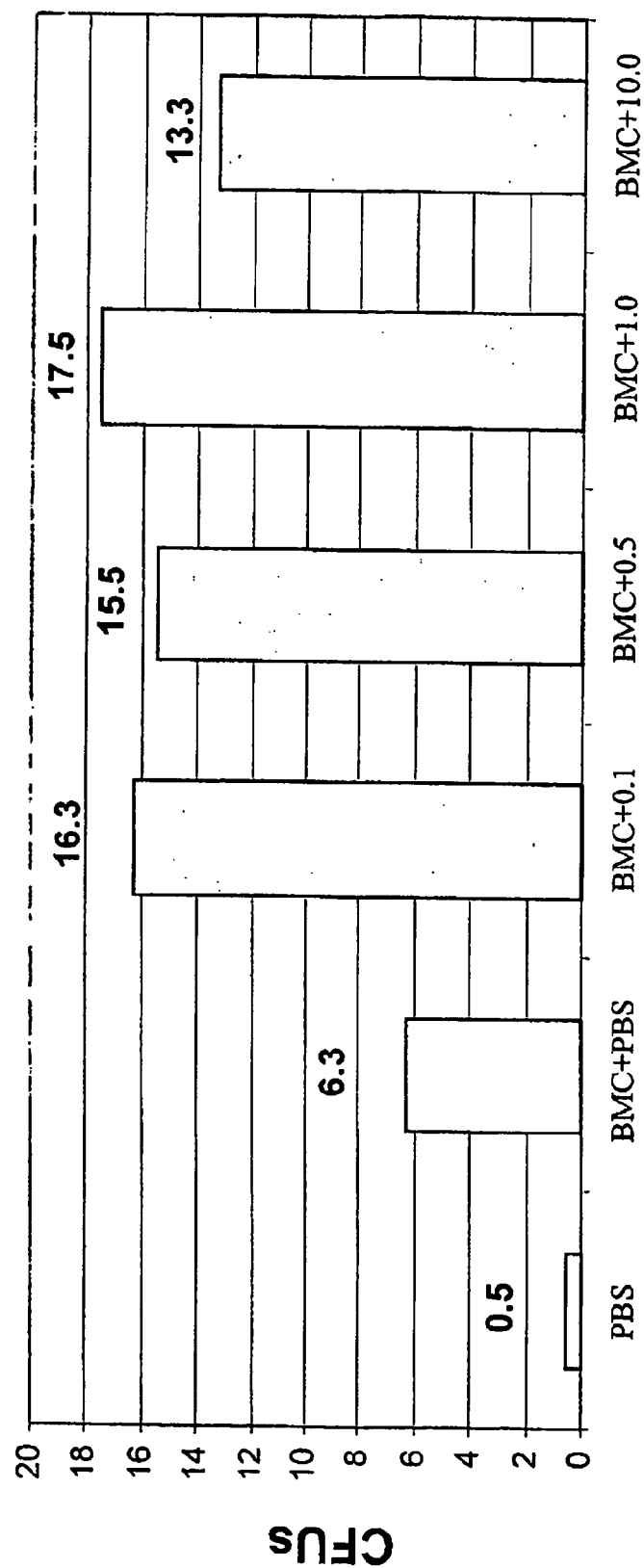

FIG. 10: Spleen CFU of irradiated mice transplanted with BMC pre-treated with FTGN.

Total body irradiated mice (7.5 Gy) were injected with $6\times10^4$ BMC previously treated with FTGN tetrapeptide at different concentrations (0.1, 0.5, 1.0 and 10.0 µg/ml). Spleen colonies were measured 9 days after irradiation and compared to PBS mice (mice transplanted with BMC incubated with PBS).

Abbreviations: Treat.: treatment; BMC: bone marrow cells; CFUs: colony forming units from spleen.

Figure 11:
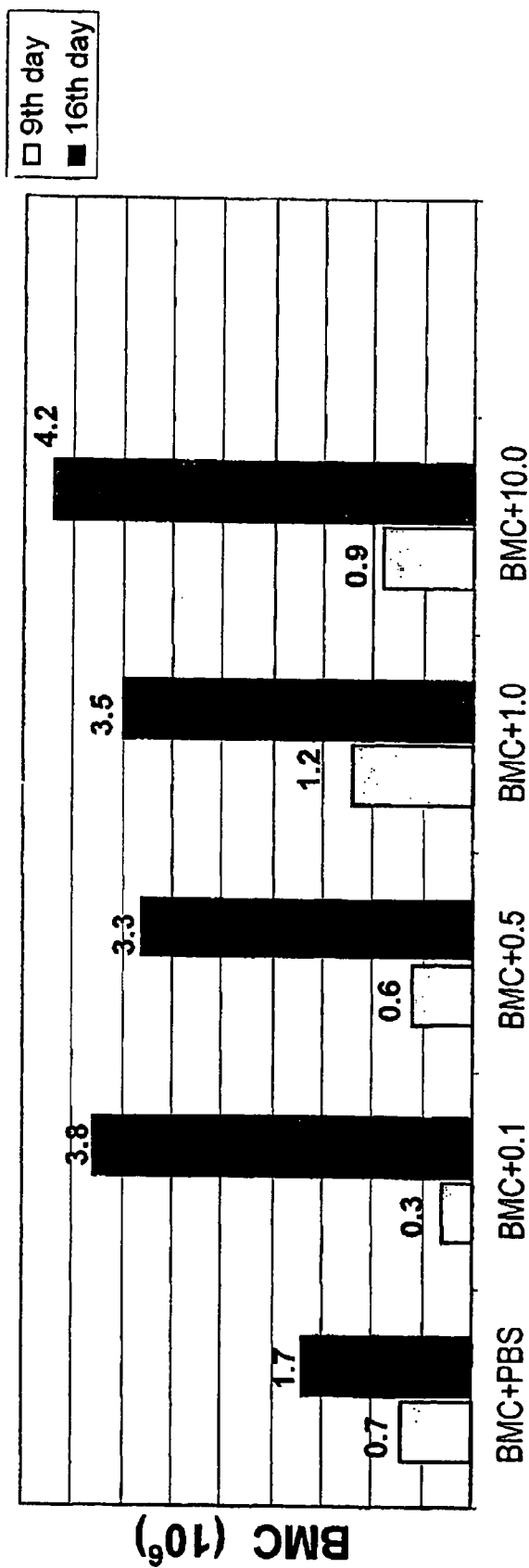

FIG. 11: BMC count in irradiated mice transplanted with BMC pre-treated with FTGN.

Total body irradiated mice (7.5 Gy) were injected with $6\times10^4$ BMC previously treated with FTGN tetrapeptide at different concentrations (0.1, 0.5, 1.0 and 10.0 µg/ml). Bone marrow cells were counted 9 (light color) and 16 (dark color) days after irradiation and compared to PBS mice (mice transplanted with BMC incubated with PBS).

Abbreviations: Treat.: treatment; BMC: bone marrow cells and BM cell count ($10^6$: millions).

Figure 12:
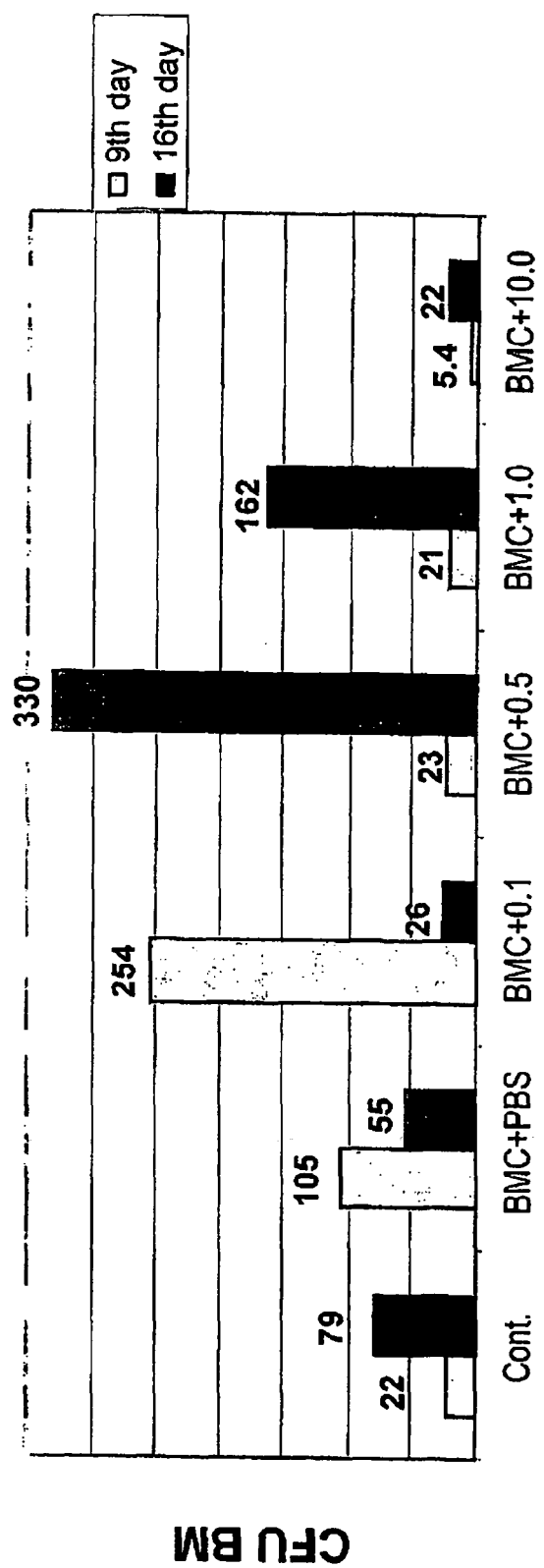

FIG. 12: Bone marrow CFU of irradiated mice transplanted with BMC pre-treated with FTGN.

FIG. 12: Bone marrow CFU

Total body irradiated mice (7.5 Gy) were injected with $6\times10^4$ BMC previously treated with FTGN tetrapeptide at different concentrations (0.1, 0.5, 1.0 and 10.0 µg/ml). BM colonies were measured 9 (light color) and 16 (dark color) days after irradiation and compared to control mice (irradiated but not transplanted mice) or PBS mice (mice transplanted with BMC incubated with PBS).

Abbreviations: Treat.: treatment; BMC: bone marrow cells; CFU BM: colony forming units from BMC; Cont.: control.

Figure 13:
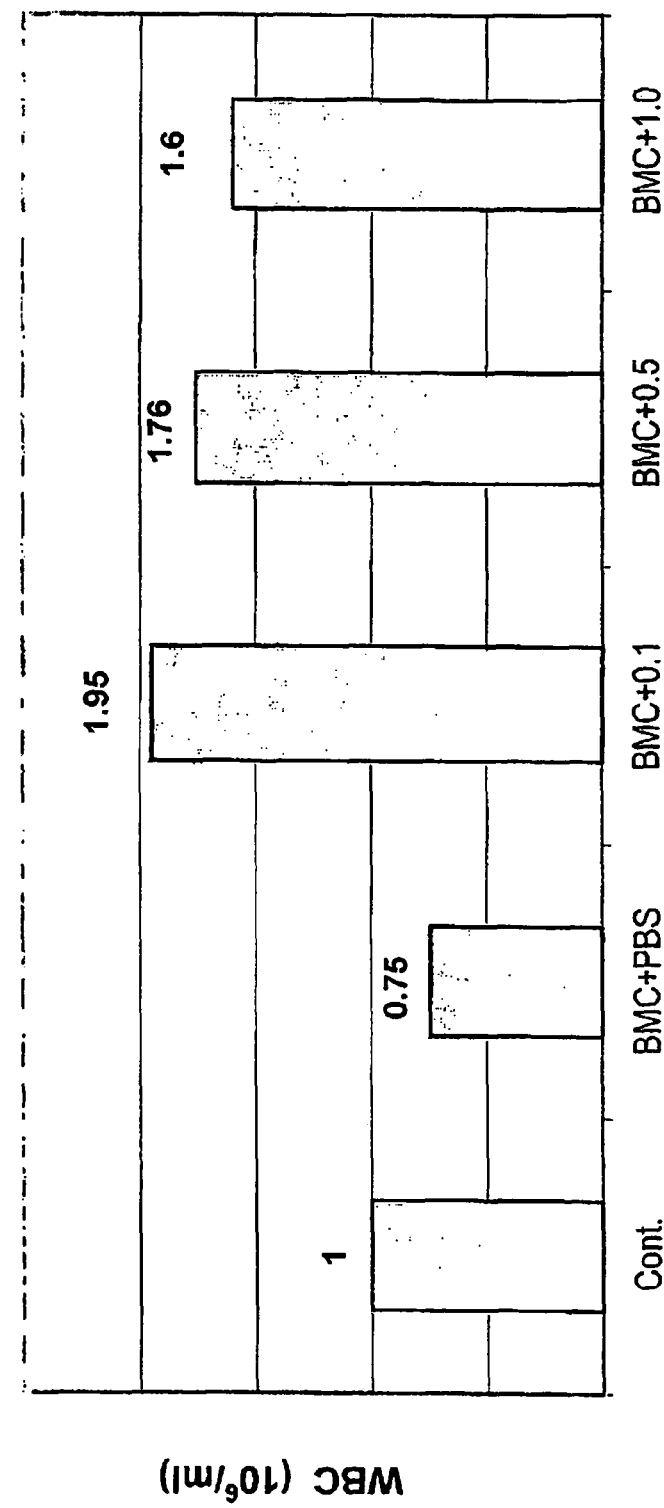

FIG. 13: WBC count in irradiated mice transplanted with BMC pre-treated with FTGN.

Total body irradiated mice (7.5 Gy) were injected with $6\times10^4$ BMC previously treated with FTGN tetrapeptide at different concentrations (0.1, 0.5, 1.0 and 10.0 µg/ml). White blood cells were counted 16 days after irradiation and compared to control mice (irradiated but not transplanted mice) or PBS mice (mice transplanted with BMC incubated with PBS).

Abbreviations: Treat.: treatment; BMC: bone marrow cells; WBC: white blood cells ($10^6$/ml); Cont.: control.

Figure 14:
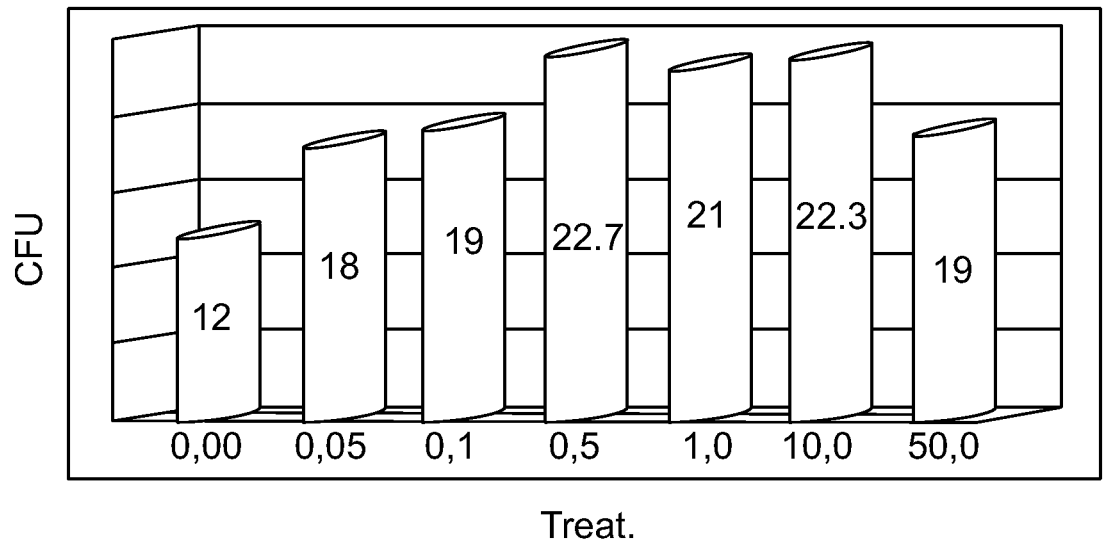

FIG. 14: Spleen CFU of irradiated mice transplanted with BMC pre-treated with various FTGN concentrations.

Total body irradiated mice (7.0 Gy) were injected with $6\times10^4$ BMC previously treated with FTGN tetrapeptide at different concentrations (0.1, 0.5, 1.0, 10.0 and 50.0 µg/ml). Spleen colonies were measured 9 days after irradiation and compared to mice transplanted with BMC incubated only with PBS.

Abbreviations: Treat.: treatment; CFU: colony forming units from spleen.

Figure 15:
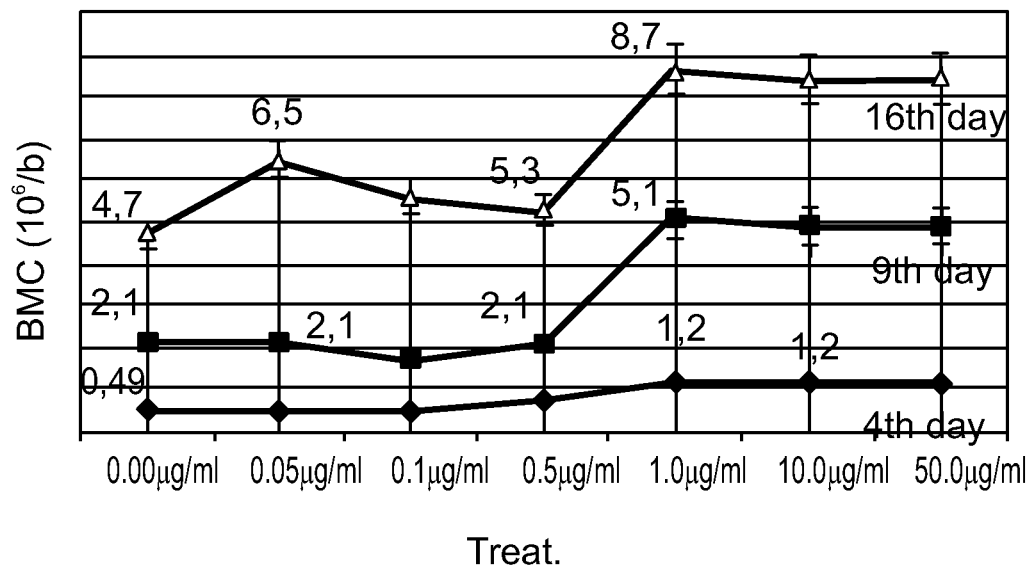

FIG. 15: BMC count in irradiated mice transplanted with BMC pre-treated with various FTGN concentrations.

Total body irradiated mice (7.0 Gy) were injected with $6\times10^4$ BMC previously treated with FTGN tetrapeptide at different concentrations (0.1, 0.5, 1.0, 10.0 and 50.0 µg/ml). Bone marrow cells from femur were counted 4, 9 and 16 days after irradiation and compared to mice transplanted with BMC incubated only with PBS.

Abbreviations: Treat.: treatment; BMC: BM cell count ($10^6$/b: millions/bone).

FIG. 16a-b: BMC count in irradiated mice transplanted with BMC irradiated/non irradiated donor cells pre-treated with FTGN.

Donor BM cells incubated ex vivo in RPMI medium in the presence (10 µg/ml) or absence of FTGN tetrapeptide for 2 hours were transplanted into irradiated recipient mice (7.0 Gy.). Twenty days after transplant BMC/bone were counted.

FIG. 16a: transplanted BM cells from irradiated (4,5 Gy) donor mice incubated in the presence (+) or absence (−) of FTGN tetrapeptide.

FIG. 16b: transplanted BM cells from non irradiated control mice incubated in the presence (+) or absence (−) of FTGN tetrapeptide.

Abbreviations: BMC: BM cell count ($10^6$/b: millions/bone).

Figure 17:
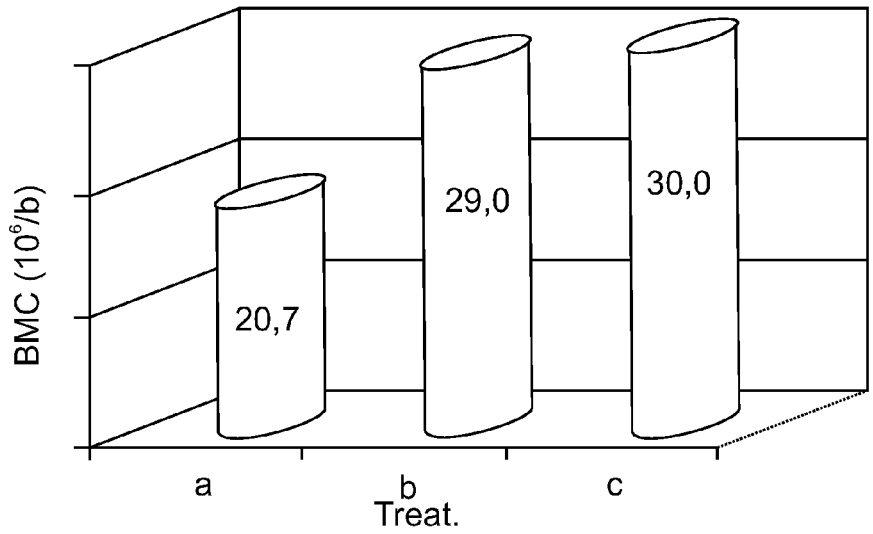

FIG. 17a-c: BMC count in irradiated mice treated with FTGN.

Irradiated mice (6,5 Gy) were treated in vivo with the FTGN tetrapeptide. Thirty days after treatment BMC were counted.

FIG. 17a: Control mice irradiated and injected with PBS.

FIG. 17b: Irradiated mice I.V. injected once with 50 ng FTGN 2 hours after irradiation.

FIG. 17c: Irradiated mice I.V. injected twice with 50 μg FTGN (each time) 2 and 24 hours after irradiation.

Abbreviations: BMC: bone marrow cell count ($10^6$/b: millions/bone); Treat.: treatment; I.V.: intravenous.

Figure 18:
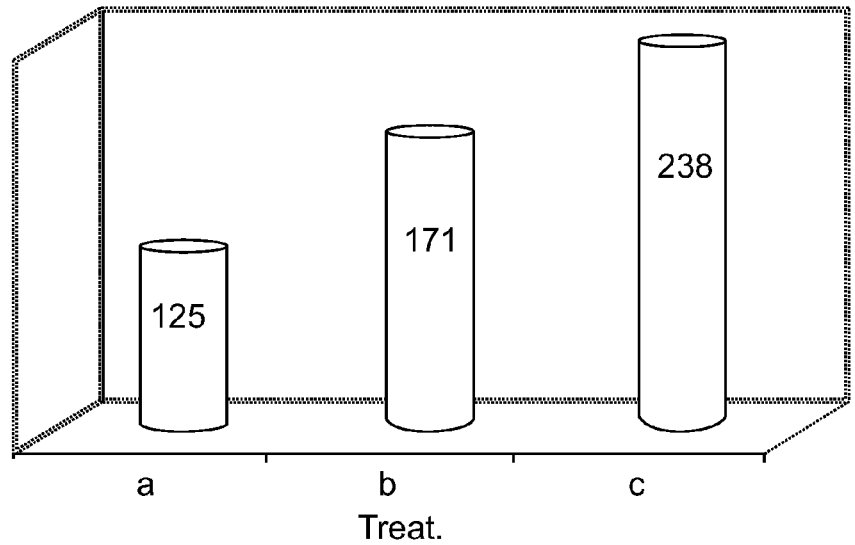

FIG. 18a-c: Bone marrow CFU count of irradiated mice treated with FTGN.

Irradiated mice (6,5 Gy) were treated in vivo with the FTGN tetrapeptide. Thirty days after treatment CFU from BM were counted.

FIG. 18a: Control mice irradiated and injected with PBS.

FIG. 18b: Irradiated mice I.V. injected once with 50 μg FTGN 2 hours after irradiation.

FIG. 18c: Irradiated mice I.V. injected twice with 50 μg FTGN (each time) 2 and 24 hours after irradiation.

Abbreviations: CFU BM: colony forming units from BMC; Treat.: treatment; I.V.: intravenous.

Figure 19:
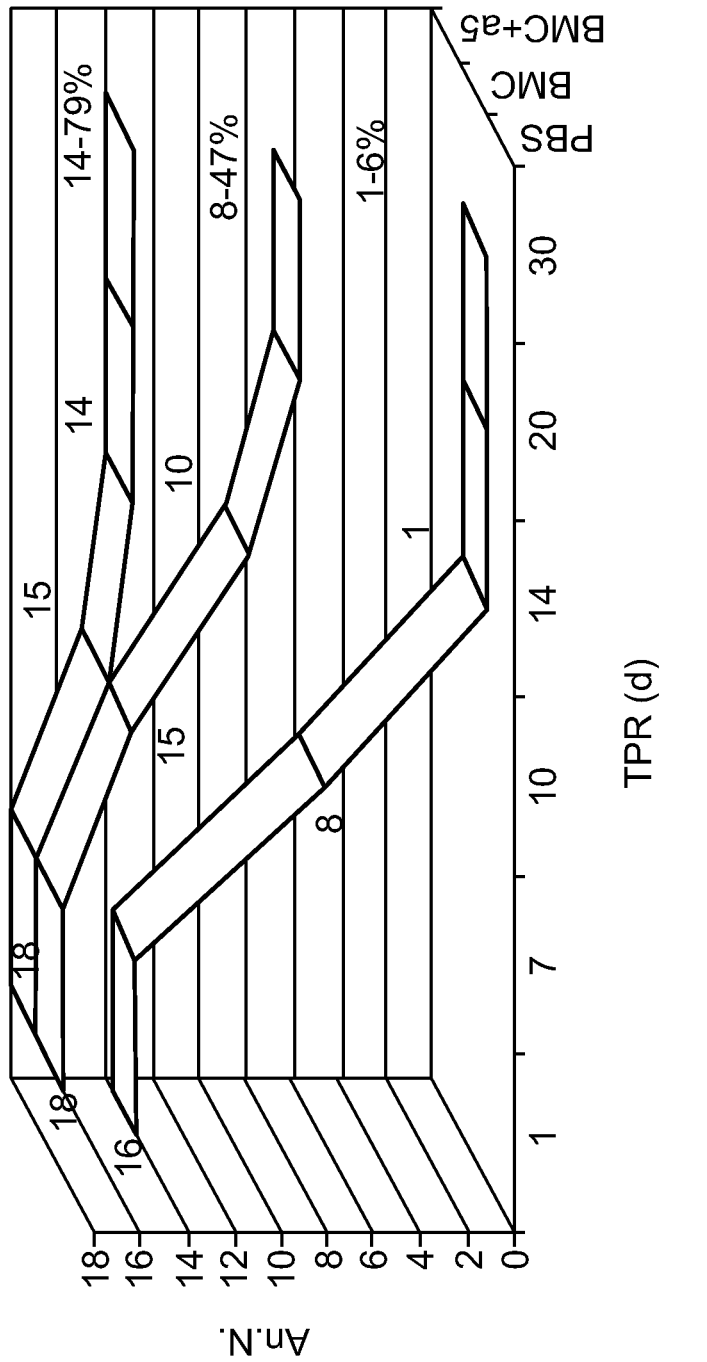

FIG. 19: Survival curve of irradiated mice transplanted with BMC pre-treated with purified a5 spleen extract subfraction.

Irradiated mice (8 Gy) were transplanted with BMC previously incubated with the spleen extract fraction a5. Mice survival was pursue during 30 days and compared to irradiated mice untreated (PBS) or mice that were transplanted with untreated donor BMC.

Abbreviations: BMC: bone marrow cells; An. N.: animal number, TPR: time post-radiation; D: days.

Figure 20:
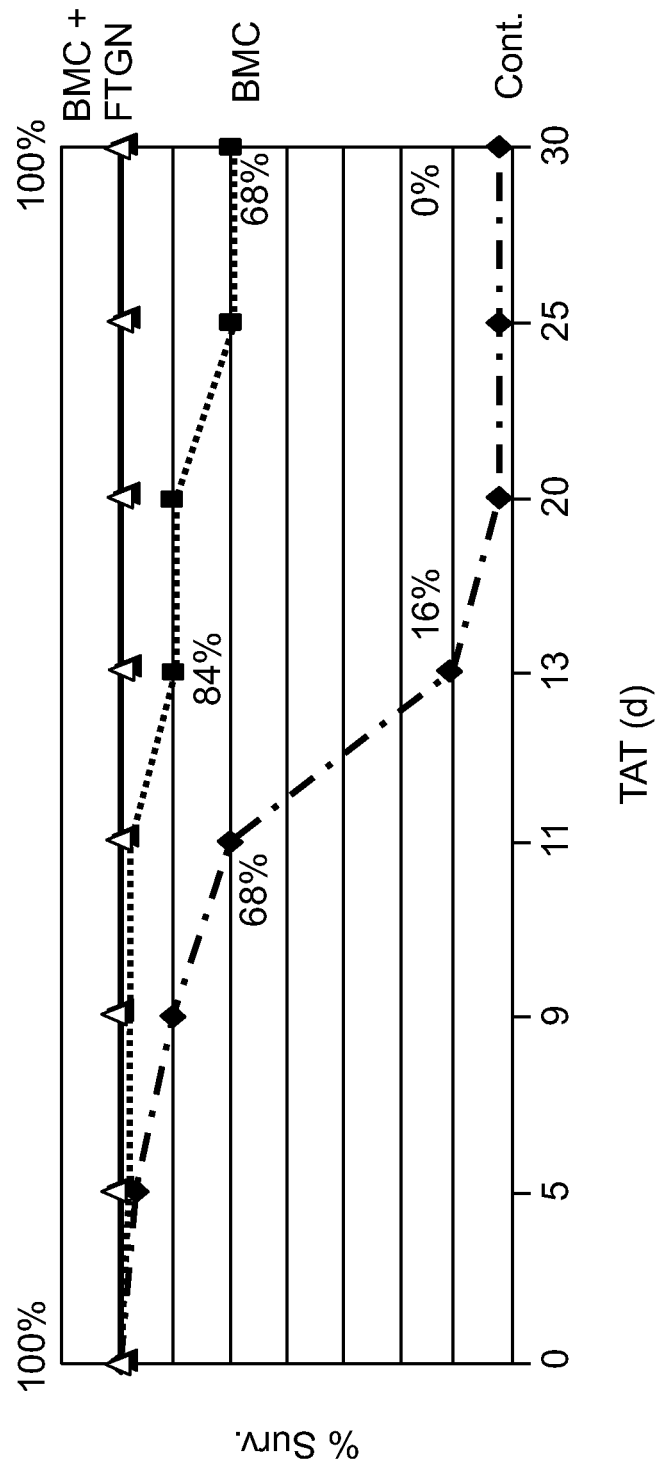

FIG. 20: Survival curve of irradiated mice transplanted with BMC pre-treated with FTGN.

Lethally irradiated mice (10 Gy.) were transplanted with 60.000 donor BM cells previously incubated for 1 hour in the presence (10 mg/ml) or absence of FTGN tetrapeptide. Mice survival was pursue during 30 days and compared to control irradiated mice untreated or mice that were transplanted with untreated donor BMC.

Abbreviations: TAT: time after treatment, D: days; % Surv.: percentage of mice survival; Cont.: control.

DETAILED DESCRIPTION OF THE INVENTION

The inventor has found that certain HPLC fractions of tortoise spleen extract have a surprisingly strong protective effect on irradiated mice, and further it has been found that said effect was related to a proteinaceous factor in said fractions. Recovery of white cells populations in surviving mice has been found to be consistently enhanced by said proteinaceous factor. The results indicated that said tortoise spleen proteinaceous factor was responsible for proliferation of undifferentiated stem cells that had survived irradiation in mice, and for their differentiation into lymphoid and myeloid cell lines, which could be observed in the bone marrow from about $8^{th}$ day post irradiation. Said factor was assumed to be responsible for the surprising radio-resistance in mice, further confirmed by the increased survival rate of the irradiated mice.

This tortoise spleen proteinaceous factor has been linked with oligopeptides of molecular weight below 2000 Daltons. In a preferred purification protocol, the extract from tortoise spleen is fractionated by protein and peptide chemistry techniques known in the art. Such peptide purification techniques may include: gel filtration chromatography, ion-exchange chromatography, affinity chromato-graphy, reverse phase chromatography, HPLC with C18 column, electrophoresis, TLC and MS.

The proteinaceous factor or the oligopeptide of this invention are obtained either by extraction from tortoise spleen, or by synthesis, using techniques known in the art of protein chemistry.

The proteinaceous factor and the oligopeptide of this invention are originated from natural compounds and therefore, they are considered non-toxic. This fact may allow the repeated use of the compounds, as needed according to the situation of the subject in need, without concern regarding secondary effects.

A tetrapeptide isolated from the HPLC fractions of the tortoise spleen extract showed the same biological properties as seen for the whole tortoise extract described above (Examples 1, 3, 4 and 5). This tetrapeptide amino acid sequence is identified as FTGN (SEQ ID: No. 1)

The term oligopeptide and tetrapeptide used through all the invention description are equally related to the synthetic FTGN (SEQ ID: No. 1) and refer to an isolated peptide.

The tetrapeptide was synthesized and it was found to support hemopoiesis in irradiated mice. Mice that were whole-body irradiated with a dose of 7.5 Gy (which is normally considered a lethal dose), were transplanted by intravenous injection with donor's bone marrow cells preincubated ex vivo with different concentrations of the synthetic tetrapeptide. The comparison between treated and untreated mice showed that tetrapeptide FTGN enhanced spleen growth, substantially enhanced the number of spleen colonies, and increased the number of bone marrow cells (BMC) and white blood cells (WBC), as described in Examples 4 and 5.

In adult mice the spleen is a hematopoietic active organ, especially following recovery from damage inflicting treatment, such as irradiation. Transplanted cells "home" to the spleen (as well as the BM) and first develop into discrete colonies, which later become confluent. This results in an increase in the spleen size. As the hematopoietic system recovers, the spleen returns into its normal size. Therefore, FTGN tetrapeptide treatment may well accelerate hematopoietic recovery of the spleen. Mice transplanted with FTGN-treated cells demonstrated an early increment in the spleen size, a faster development of spleen colonies and an earlier normalization of the spleen size.

It is understood that all proteinaceous tortoise spleen factors supporting hemopoiesis, irrespective of their derivation, are a part of this invention. It is further understood that any tortoise-derived proteinaceous composition is a part of this invention, which comprises a peptide or protein comprising amino acid sequence FTGN, or its variants maintaining the above described protective activity or a derivative thereof or a modification maintaining the above described protective activity, i.e. functional derivatives. Said functional derivatives or modifications may include, but are not limited to, chemical modifications, such as substitution of side chains of amino acids, or alternatively modification of the terminal carboxyl or amino groups or internal hydroxyl, wherein the modification may comprise amidation, esterification, and alkylation. Said modification may, e.g., modulate the biological activity, or improve stability, such as in vivo stability in plasma after injection or chemical stability, or otherwise. An oligopeptide, comprising in its sequence tetrapeptide FTGN, preferably having molecular weight lower than 2000 Daltons, and exhibiting said protective activity, is a part of this invention. Said variant may comprise an alteration in the side chain of one amino acid in said tetrapeptide resulting either from in vivo mutation or from chemical modification in vitro. Said oligomer may comprise a dimer or oligomer of said tetrapeptide FTGN.

In still another embodiment, this invention is directed to a variant, modification, or a derivative of tetrapeptide FTGN, to its physiologically acceptable salt, ester or amide that stimulates the proliferation in vitro of bone marrow cell precursors (and/or bone marrow stem cells). Donor bone marrow cells precursors (and/or marrow stem cells) that are treated with the oligopeptide before transplantation can thus proliferate after their transplantation into an irradiated mammal recipient (Example 7).

In another embodiment, this invention provides an oligopeptide extracted from tortoise spleen, which enhances hemopoiesis in a mammal by stimulating ex vivo/in vitro BMC-precursors (and/or bone marrow stem cells). Thus, donor BMC-precursors (and/or bone marrow stem cells) can be ex vivo treated with the oligopeptide of the invention before transplantation into said mammal. An oligopeptide of this embodiment of the present invention protects an irradiated mammal and enhances its survival rate by exposing its own hemopoietic cells, or donor's hemopoietic cells to the effect of said oligopeptide.

As used herein, "precursors or progenitor cell" refers to any somatic cell, which has the capacity to generate fully differentiated, functional progeny by differentiation and proliferation. Hematopoietic progenitor cells include those cells, which are capable of successive cycles of differentiating and proliferating to yield up to eight different mature hematopoietic cells lineages. At the most primitive or undifferentiated end of the hematopietic spectrum, hematopoietic progenitor cells include the hematopietic "stem cells." These rare cells, which represent 1 in 10,000 to 1 in 100,000 of cells in the bone marrow, each have the capacity to generate $>10^{13}$ mature blood cells of all lineages and are responsible for sustaining blood cell production over the life of an animal.

A "hematopoietic stem/progenitor cell", is a cell which is able to differentiate to form a more committed or mature blood cell type. A "hematopoietic stem cell" or "stem cell" is one that is specifically capable of long-term engraftment of a lethally irradiated host.

It is an object of the present invention to provide a method for enhancing the proliferation and/or differentiation and/or maintenance of primitive hematopoietic cells. Such a method may be useful for enhancing repopulation of hematopoietic stem cells and thus mature blood cell lineages. This is desirable where a mammal has suffered a decrease in hematopoietic or mature blood cells as a consequence of an accident, radiation or chemotherapy.

In a specifically preferred embodiment, the composition of the invention is intended for supporting bone marrow transplantation. This effect is due to the activity of the oligopeptide that increases proliferation of stem cells, accelerating the hematological reconstruction upon bone marrow transplantation and increasing the cellularity of bone marrow.

As described in Examples 4 and 5, the oligopeptide of the invention has been found to enhance hematopoietic reconstruction. The aim of all BMTs is to replace the host hematopoietic stem cells injured. These stem cells can replicate repeatedly and differentiate to give rise to the whole variety of cells.

In addition, the oligopeptide described herein may be used in the preparation of pharmaceutical compositions enhancing proliferation of transplanted stem cells enabling successful transplantation even when using a reduced donor's cell number. Increasing the number of hematopoietic stem cells can be achieved by ex vivo/in vitro treatment of donor's cells prior to transplantation or by in vivo treatment of recipient prior or concomitant with the BM transplant procedure.

More specifically, the invention provides for the use of this tetrapeptide in the preparation of a pharmaceutical composition for supporting bone marrow transplantation. This effect is due to the activity of the oligopeptide in increasing proliferation of stem cells, accelerating the hematological reconstruction upon bone marrow transplantation and increasing the cellularity of bone marrow.

In another aspect, the present invention relates to the use of the above described oligopeptide in the preparation of a pharmaceutical composition for enhancement of bone marrow transplant success, hematopoietic reconstruction, bone marrow re-population particularly after high dose of cytotoxic exposure, said such exposure results from a conventional chemotherapy or irradiation treatment or an accidental event. Bone marrow transplant donor cells may be from autologous origin (autologous stem cells) or allogeneic from a compatible sibling or a matched unrelated donor.

The pharmaceutical compositions of the invention comprise as active ingredient an oligopeptide as described above, in a pharmaceutically acceptable carrier, excipient or stabilizer, and optionally other therapeutic constituents. Acceptable carriers, excipients or stabilizers are non-toxic to recipients at the dosages and concentrations employed, and include buffers, such as phosphate buffered saline and like physiologically acceptable buffers, and more generally all suitable carriers, excipients and stabilizers known in the art, e.g., for the purposes of adding flavors, colors, lubrication, or the like to the pharmaceutical composition.

Therapeutic formulations of the oligopeptide are prepared for storage by mixing this tetrapeptide having the desired degree of purity with optional physiologically acceptable carriers, excipients, protease inhibitors or stabilizers. For ex vivo and in vitro treatment the tetrapeptide may be stored lyophilized or frozen after reconstitution in sterile water or other physiological buffer.

Carriers may include starch and derivatives thereof, cellulose and derivatives thereof, e.g., microcrystalline cellulose, Xantham gum, and the like. Lubricants may include hydrogenated castor oil and the like.

A preferred buffering agent is phosphate-buffered saline solution (PBS), which solution is also adjusted for osmolarity.

A preferred pharmaceutical formulation is one lacking a carrier. Such formulations are preferably used for administration by injection, including intravenous injection.

The pharmaceutical composition of the invention may comprise additional active agents selected from growth factors, anti-rejection or tolerance inducing agents. Additional included active agents of the composition may be selected from the analgesic, antibiotic, anti-inflammatory, antineoplastic, cyto-protectant, glucocorticoid, hematopoietic, and immunosuppressant groups.

The preparation of pharmaceutical compositions is well known in the art and has been described in many articles and textbooks, see e.g., Remington's Pharmaceutical Sciences, Gennaro A. R. ed., Mack Publishing Company, Easton, Pa., 1990, and especially pages 1521-1712 therein.

The oligopeptide or the pharmaceutical compositions to be used for in vivo administration must be sterile. This is readily accomplished by filtration through sterile filtration membranes, prior to or following lyophilization and reconstitution. Oligopeptide may be stored in solution. Therapeutic oligopeptides compositions generally are placed into a container having a sterile access port, for example, an intravenous solution bag or vial having a stopper pierceable by a hypodermic injection needle.

Any suitable route of administration may be employed for providing a mammal, especially a human, with an effective dosage of a tetrapeptide of this invention.

The pharmaceutical compositions of the invention can be prepared in dosage units forms. The dosage forms may also include sustained release devices. The compositions may be prepared by any of the methods well known in the art of pharmacy. Such dosage forms encompass physiologically acceptable carriers that are inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG.

For all administrations, conventional depot forms are suitably used. Such forms include for example, microcapsules, nano-capsules, liposomes, inhalation forms, nose sprays and sustained-release preparations.

Suitable examples of sustained-release preparations include semi-permeable matrices of solid hydrophobic polymers containing the oligopeptide according to the invention, which matrices are in the form of shaped articles, e.g. films, or micro-capsules. Examples of sustained-release matrices include polyesters, hydrogels, polylactides as described by, (U.S. Pat. No. 3,377,919), copolymers of L-glutamic acid and ethyl-L-glutamate, non-degradable ethylene-vinyl acetate, degradable lactic acid-glycolic acid copolymers such as the Lupron Depots™ (injectable microspheres composed of lactic acid-glycolic acid copolymer and leuprolide acetate), and poly-D-(–)-3-hydroxybutyric acid. While polymers such as ethylenevinyl acetate and lactic acid-glycolic acid enable release of molecules for over 100 days, certain hydrogels release proteins for shorter time periods.

Sustained-release oligopeptide and particularly the FTGN compositions may be liposomally entrapped. Liposomes containing this oligopeptide are prepared by methods known in the art, such as described in Eppstein, et al., Proc. Natl. Acad. Sci. USA (1985) Vol. 82:3688; Hwang, et al., Proc. Natl. Acad. Sci. USA (1980) Vol. 77:4030; U.S. Pat. Nos. 4,485,045 and 4,544,545. Ordinarily, the liposomes are the small (about 200-800 Angstroms) unilamellar type in which the lipid content is greater than about 30 mol. % cholesterol, the selected proportion being adjusted for the optimal polypeptides therapy. Liposomes with enhanced circulation time are disclosed in U.S. Pat. No. 5,013,556.

Although all the above mentioned techniques might be use to deliver the pharmaceutical composition to a subject in need, intravenous and oral administration may be preferred.

The pharmaceutical composition may be administered to a subject in need, in a single or multiple occasions. The "effective treatment amount" of the oligopeptide or the compositions of the invention is determined by the severity of the damaged caused to the BMC (by accident or intentionally as a manner of radiotherapy) in conjunction with the therapeutic objectives, the route of administration and the patient's general condition (age, sex, weight and other considerations known to the attending physician).

Accordingly, it will be necessary for the therapist to titer the dosage and modify the route of administration as required to obtain the optimal therapeutic effect. Typically, the clinician will administer the oligopeptide in increasing dosages until the desired effect is achieved.

For therapeutic applications, the oligopeptide or the pharmaceutical composition useful according to the invention are administered to a mammal, preferable a human, in a physiologically acceptable dosage from, including those that may be administered to a human intravenously as a bolus or by continuous infusion over a period of time. Alternative routes of administration include intramuscular and intraperitoneal.

The preferably single dosage comprises an amount of 1-10 mg of active ingredient/Kg body weight for in vivo treatment. The preferred concentration of the oligopeptide in the medium that stimulates BMC is and 1-10 µg/ml and this concentration is recommended for ex vivo or in vitro incubation.

In a broader aspect, the present invention provides a method that enhances the bone marrow transplant success, the hematopoietic reconstruction, and the bone marrow re-population, after being exposed to a high dose of radiation. This method comprises administering to a cell or to a subject in need thereof, an effective amount of the tetrapeptide having stimulatory activity on hematopoietic cells as described above, or of a composition of the invention.

A preferred embodiment relates to a method for enhancing the proliferation of hematopoietic stem/progenitor cells. According to the invention, this method comprises the steps of exposing these cells to an effective amount of an oligopeptide having stimulatory activity on hematopoietic cells, or to an effective amount of a composition comprising the same, as described above. According to the invention such exposure is effective in enhancing the proliferation of said cells.

The term "enhancing proliferation of a cell" encompasses the step of increasing the extent of growth and/or reproduction of the cell relative to an untreated cell either in vitro/ex vivo or in vivo. An increase in cell proliferation in cell culture can be detected by counting the number of cells before and after exposure to a molecule of interest. The extent of proliferation can be quantified via microscopic examination of the degree of confluency.

The method of the invention may be used as an in vivo method of treatment, in case that the treated cells are present in a mammal.

In vivo treatment according to the invention relates to a method for re-populating blood cells in a mammal. This method comprises the steps of administering to said mammal a therapeutically effective amount of an oligopeptide having stimulatory activity on hematopoietic cells as described above, or of a composition comprising the same. These hematopoietic cells may be erythroid, myeloid or lymphoid cells.

"Treatment" refers to therapeutic treatment. Those in need of treatment are mammal subjects with a low hematopoietic cell count, a consequence of a radiation exposure resulting from a programmed medical treatment or an accident.

"Mammal" for purposes of treatment refers to any animal classified as a mammal including, human, research animals, domestic and farm animals, and zoo, sports, or pet animals, such as dogs, horses, cats, cows, etc. Preferably, the mammal is human.

For treating a subject carrying a transplant, an ex vivo method may be adopted. In this method, the cells intended for transplantation are exposed to effective amount of the oligopeptide or compositions of the invention, prior to their transplantation.

As described in Example 7, such strategy was remarkably effective. A short ex vivo treatment of the transplanted cells with the tetrapeptide, improved the survival rate of the irradiated mice to 100%.

A combined ex vivo/in vivo approach may provide the basis for a forward-looking strategy for (i) obtaining small stem cell preparations from donors blood or marrow and (ii) enabling healthy individuals to have their stem cells stored for a time when the cells might be needed to treat a serious condition, thus bypassing the complexity associated with the use of allogeneic BMT.

This invention is also directed to a method of reducing the detrimental effect of ionizing radiation on tissue or body of a subject, comprising exposing hemopoietic cells to oligopeptide derived from tortoise, wherein said exposing may be carried out ex vivo, in vitro, or in vivo. In nitro/ex vivo exposure may comprise treating donor's hemopoietic cells with said oligopeptide. In vivo exposure may comprise treating hemopoietic cells of the irradiated subject with said oligopeptide, wherein said oligopeptide is administered to said subject.

In another embodiment of this invention, a method of reducing the detrimental effect of ionizing radiation on tissue or body of a subject comprises a synthetic oligopeptide comprising sequence FTGN.

In one aspect, this invention provides a peptide comprising sequence FTGN, preferably a peptide consisting of the sequence FTGN, particularly for use as a radioprotective agent which can be administered before the radiation, wherein said radiation can be a part of a therapy. In another aspect, this invention provides a peptide comprising or consisting of the sequence FTGN for use as a radioprotective agent which can be administered after the irradiation, wherein said irradiation can be an accidental event. A composition comprising said peptide may be administered by injection, for example intravenously, intraperitoneally, subcutaneously, comprising a dose of about 1-10 mg/kg body weight.

The term radiation used in the invention refers to any high-energy radiation source, said such radiation comes from x-rays, gamma rays, or particles such as neutrons and electrons. Radiation may come from a machine outside the body (external-beam radiation therapy), or it may come from radioactive material inserted into the body near cancer cells (internal radiation therapy, implant radiation, or brachytherapy). It also may include systemic radiation therapy which uses a radioactive substance, such as a radiolabeled monoclonal antibody, that circulates throughout the body (radiotherapy).

This invention further relates to the use of an oligopeptide extracted from tortoise spleen or a synthetic peptide homologous thereto, in the preparation of a pharmaceutical composition or medicament for treating or preventing damage to a tissue or body caused by cytotoxic agents selected from ionizing radiations and cytotoxic chemicals. In one embodiment of the use according to this invention, the cytotoxic agent comprises a radiation that is a part of a therapy or accidental. In another embodiment, said cytotoxic agent is a part of chemotherapy.

The pharmaceutical composition of the invention may therefore be intended for increasing the white blood cells (WBC), hematopoietic stem cells in peripheral blood (PBL), and overall bone marrow cellularity.

The oligopeptide or the composition of the invention are useful in in vivo or ex vivo enhancing proliferation and/or differentiation and/or maintenance of hematopietic stem/progenitor cells, expand population of these cells and enhance repopulation of such cells and blood cells of multiple lineages in a mammal.

It would therefore be of therapeutic importance to use small peptides such as the oligopeptide described in the present application, that stimulate post-BMT hemopoietic reconstruction by enhancing in vivo, ex vivo and/or in vitro the hemopoietic microenvironment.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The invention will be further described and illustrated in the following examples. The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the intended scope of the invention.

EXAMPLES

Materials and Methods

1. Tortoise Spleens Extract Preparation

Spleen extracts were prepared from 6-10 years old *Testudo horsfieldi*, Tortoise from Uzbekistan and Kazakhstan.

Figure 1:
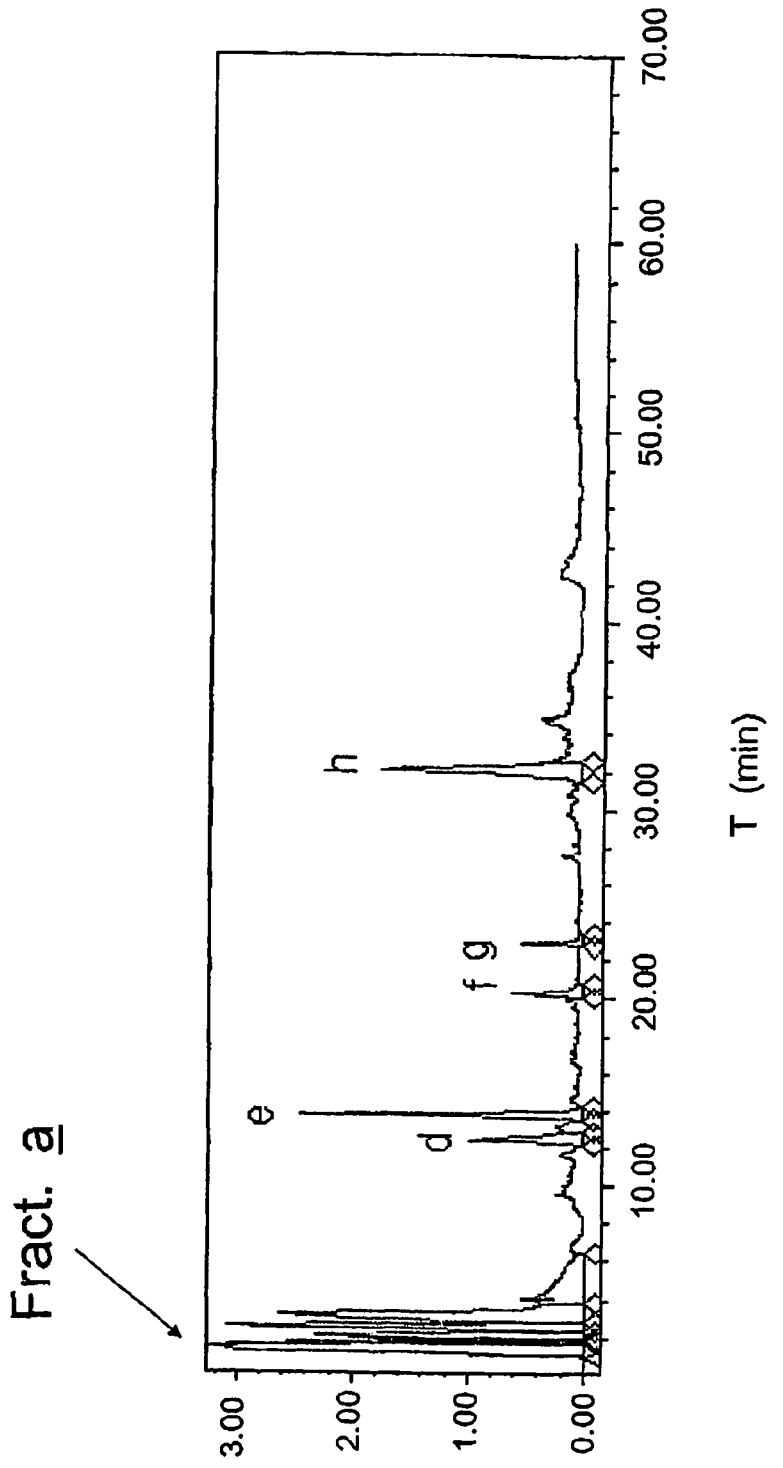
FIG. 1: HPLC chromatogram of tortoise spleen extract

Crude extract of tortoise spleen was prepared from 200 tortoises. The animals were sacrificed by decapitation, and the spleens were collected in a dish placed into liquid nitrogen bath. Deep frozen tissue was crushed to powder. One liter of PBS containing protease inhibitor cocktail was added to powder, placed at 4° C. for 24 hours, and centrifuged twice at 4400 g for 30 min. The supernatant was lyophilized. To remove hemoglobin from the above crude extract, the powder extract was dissolved in distilled water to a concentration of 50 mg/ml and cooled in ice/water bath. Ethanol/chloroform (2/1) was added drop-wise to the mixture, 2 ml per 1 ml of mixture. After mixing for 20 min, the mixture was centrifuged at 0° C. for 30 min. Supernatant was separated and lyophilized. The powder was dissolved in superpure distilled water to a concentration of 40 mg/ml. After filtration by Syringe filter (Nylon 0.45 mcm) the mixture was applied onto a preparative HPLC C18 column (Vydac 218TP, 250×12 mm) (FIG. 1).

2. Tortoise Spleens Extract Fractions Purification

The peaks from 20 batches of HPLC described above (FIG. 1) were pooled and characterized by the MALDI-TOFF mass spectra analysis and by NMR, and by measuring their biological activities.

Active fractions were re-purified on preparative HPLC column C18 to yield six peaks (denoted a1 to a6 in FIG. 4). Proteinaceous fraction a5 was found to be most active. The results of TLC (Silica Gel 60F254) of fractions a4 to a6 were developed by ninhidrin, together with free amino acids Glu, Val, Gly, and Met, are shown in FIG. 5. Fraction a5 indicates the presence of a heavier peptidic component (near the start). This fraction was collected from several runs, and pooled. A peptide of molecular weight 437.45 (MS) was identified. Sequencing by the Edmann method (carried out at the Weizmann Institute in Rehovot, Israel) showed tetrapeptide FTGN.

3. Tetrapeptide FTGN Synthesis

Tetrapeptide FTGN was synthesized by the solid phase peptide synthesis method, using the 9-fluorenylmethoxycarbonyl (FMOC) strategy. FITC was assembled with a handle (e-aminocaproic acid). The peptides were then cleaved from the resin with trifluoroacetic acid solution. Finally the peptides were purified on reverse phase HPLC, dry freeze and stored at −10° C.

The oligopeptide was synthesized at Sigma-Aldrich (Israel).

4. Animals

Five weeks old male C57Bl/6J mice were used as bone donors for BMC preparation. Mice from the same batches were irradiated and used as BMC recipients.

Mice were subjected to sub-lethal and lethal radiation doses (from 4.5-10 Gy) according to the experiment design.

5. Biological Methods

The biological activities of this synthesized oligopeptide were studied at the Department of Hematology of the Hadassah University Hospital, Jerusalem.

a) Bone Marrow Cell Collection

Mice femurs were removed and placed in PBS solution. Cell suspensions of bone marrow were prepared by washing each cavity of the femur with 2.0 ml PBS with a sterile syringe and 26-gauge needle. Bone marrow cell counts were obtained using a hemocytometer. Viability was assessed by Trypan blue.

b) Bone Marrow Cells Transplant

Bone marrow cells (BMC) were transplanted into mice by intravenous injection, usually 60,000 cells in 0.3 ml of PBS buffer after 2 hours incubation at 37° C. with the examined agent.

c) Mice Spleen Colonies Assessment

Mice spleen colonies (CFUs) were counted using the method of Till and McCulloch [Till J. E. and McCulloch E. A. Radiation Res. (1961) 14: 213] on 9th, 11th and 14th days after irradiation. CFUc were assayed in semi-solid medium using $2 \times 10^4$ cells/plate.

Example 1

Biological Activity of the HPLC Fractions Isolated from Spleen Extract

The tortoise spleen extract HPLC purified fractions (FIG. 1) were tested for their biological activity. Irradiated mice (6 Gy) were injected intraperitoneally with 2 μg of the different fractions. The hematopoietic activity in these mice was examined by the number of spleen endocolonies formation and by bone marrow smear preparations at the 14th day post-irradiation. Fraction d stimulated the growth of spleen endocolonies but showed no influence on the BMC. Injection of fractions e or f resulted in the same lack of effect as seen in the control mice group injected with PBS; no biological influence was observed. Fraction g did not increase the number of the spleen colonies but showed some influence on the BMC. Fraction h exerted activity on both tested parameters: it helped in the repopulation of BM and increased the number of spleen forming colonies (FIG. 2). Further HPLC mass spectra analysis of the fractions g and h revealed a peak similar to a 8450 Daltons polypeptide. Sequencing analysis of this polypeptide revealed that it resembled the ubiquitin molecule, well known to be involved in many cell processes such as in the regulation of the cell cycle, DNA repair, embryogenesis, regulation of transcription, and apoptosis.

Ex vivo treatment of donor BM cells with purified spleen extract fraction a and transplantation into irradiated mice, showed a significant influence on the BM cell restoration as seen in FIG. 3. Additional purification of fraction a (described above in methods, FIG. 4) identified the subfraction a5, as the responsible for the biological activity previously described.

Furthermore, irradiated mice transplanted with BMC treated with purified subfraction a5, increased their survival rate as evaluated 30 days post-irradiation (FIG. 19). TLC (FIG. 5) and sequencing analysis of the a5 subfraction identified the tetrapeptide FTGN as the active factor.

Example 2

Physical Characteristic of FTGN Oligopeptide

Dry freeze long term storage of the FTGN oligopeptide preserved its structural (FIG. 6a) and biological activities. The dry frozen tetrapeptide conserved its physical characteristics after reconstitution in purified water or serum (FIG. 6c) and was stable after four hours of incubation at 37° C.

Example 3

Biological Activity of FTGN Tetrapeptide Tested In Vitro

Bone marrow cells from normal (non irradiated) mice ($4\text{-}6 \times 10^6$ cells/nil) were incubated for 2 hours with 10 μg/ml tetrapeptide; the cells were washed and cloned in cytokine-supplemented methylcellulose semi-solid medium.

Myeloid colonies formed after two weeks were counted. As seen in FIG. 7a, a short in vitro incubation of bone marrow cells with the tetrapeptide resulted in an increased colony number.

Similarly, in vivo and ex vivo irradiated cells (4.5 Gy intensity) incubated for 2 hours with 10 μg/ml FTGN tetrapeptide and treated as described above, formed a larger number of colonies compared to cells that underwent the same irradiation treatment but were not brought in contact with the tetrapeptide (SEQ ID: No. 1) (FIGS. 7b and 7c).

The presence of the tetrapeptide stimulates hematopoiesis and helps restore the growth of damaged cells lineages.

Example 4

Ex Vivo BMC Treatment with FTGN Tetrapeptide

In an attempt to assess the most favorable ex vivo treatment conditions needed in order to obtain a maximal bone marrow recovery of BM transplanted irradiated recipients, the following experiments were performed.

Donor normal BMC ($4\text{-}6 \times 10^6$ cells/ml) from C57 Bl/6J mice were incubated with different concentrations of FTGN tetrapeptide (0.05; 0.1; 0.5; 1.0; 10 and 50 μg/ml) for two hours. Whole body irradiated (7.0 Gy) C57Bl/6J mice were intravenously injected with $6 \times 10^4$ treated or control cells. The recovery of the hematopoietic system in the transplanted mice was evaluated from the $4^{th}$ to the $30^{th}$ day post-irradiation.

Spleen Morphology, Weight and CFUs:

No difference in the spleen weight was observed in the $4^{th}$ day after transplantation between the control or the experimental groups (FIGS. 8 and 9).

By the $9^{th}$ day the spleen weight, as well as the spleen colonies number, was augmented in mice transplanted with FTGN tetrapeptide treated cells (FIGS. 8a and 10) in comparison to the spleens of mice transplanted with non-treated cells (FIGS. 8b and 10).

In contrast, by the $16^{th}$ day, the spleen weight of the experimental group was lower and the spleen surface was smoother relatively to the control group (FIG. 8b).

These results suggest that FTGN tetrapeptide treatment may well accelerate hematopoietic recovery of the spleen.

Mice transplanted with FTGN-treated cells demonstrated an early increase in spleen size and faster development of spleen colonies followed by an earlier normalization of the spleen size.

The total number of nucleated bone marrow cells per femur on the 16$^{th}$ day was doubled in the animals transplanted with BM cells treated with FTGN oligopeptide (FIG. 11); colony-forming cells (CFUbm) in the bone marrow assayed in semi-solid medium on the 9th and the 16th day showed an improvement when low concentrations of the oligopeptide were used (FIG. 12). The peripheral blood white cells counts (WBC) calculated on the 16$^{th}$ day were improved in all the mice transplanted with FTGN treated cells (FIG. 13).

Example 5

Optimal FTGN Tetrapeptide Treatment Concentration

In order to elucidate the optimal FTGN tetrapeptide treatment concentration needed to achieve maximum recovery of radiation damaged BMC, two sets of donor cells were examined. Donor BMC (4-6×10$^6$ cells/ml) from normal untreated C57 Bl/6J mice and from in vivo irradiated mice (4.5 Gy) collected 24 hours post-irradiation, were incubated for two hours with different concentrations of FTGN tetrapeptide (0.05; 0.1; 0.5; 1.0; 10 and 50 μg/ml). Whole body irradiated (7.0 Gy) C57Bl/6J mice were intravenously injected with 6×10$^4$ of each different donor treated cells or with control cells. The recovery of the hematopoietic system in the transplanted mice was evaluated from the 4th to the 30$^{th}$ day post-irradiation.

The highest spleen colony forming units (CFUs) count, by the 9$^{th}$ day (FIG. 14), and the greatest number of nucleated cell in BM of transplanted mice (4, 9 and 16 days after irradiation; FIG. 15) was obtained with a dose of 1-10 μg/ml of FTGN tetrapeptide ex vivo treatment.

Figure 16:
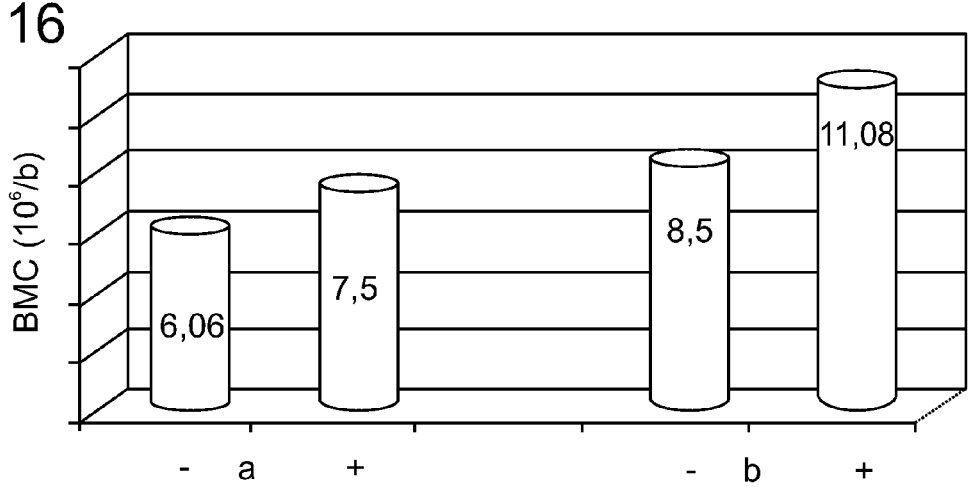

The FTGN tetrapeptide ex vivo treatment accelerated the BM repopulation activity after transplant regardless if the donor's cells were normal or originated in an irradiated mouse (FIG. 16).

The ex vivo treatment of donor cells with the tetrapeptide increased their potential to repopulate the BM and spleen of lethally irradiated mice.

Example 6

In Vivo Treatment with FTGN Tetrapeptide

Irradiated mice (6.5 Gy) were treated with one or two intravenous 50 μg FTGN tetrapeptide injections (2 or 2 and 24 hours post-irradiation). BM nucleated cells count (FIG. 17) and CFUc (FIG. 18) were examined one month later. Treatment with the FTGN tetrapeptide increased the BM repopulation in mice damaged by ionizing radiation.

Example 7

Survival of Lethal Irradiated Mice Transplanted with BM Cells Treated with Spleen Extract Fraction a5 or FTGN Tetrapeptide Irradiated mice (8 Gy) were transplanted with donor BM cells treated with the purified spleen extract subfraction a5. Mice survival, as resumed after 30 days, was improved by about 30% in the mice group injected with the treated BMC (FIG. 19).

In a further experiment, using more extreme irradiation conditions and the purified FTGN oligopeptide, even more remarkable results were achieved.

Mice irradiated with a high lethal dose (10 Gy) were injected with 6×10$^4$ cells previously incubated for one hour with 10 μg/ml FTGN tetrapeptide. Mice survival was surveyed for a 30 days period post-transplant. As seen in FIG. 20, the FTGN oligopeptide treatment ensured a 100% survival.

The results show a remarkable hemopoietic activity of the peptide according to this invention.

While this invention has been described in terms of some specific examples, many modifications and variations are possible. It is therefore understood that within the scope of the appended claims, the invention may be realized otherwise than as specifically described.

---

---

What is claimed is:

1. A method of reducing a detrimental effect of a cytotoxic factor in a subject exposed to the cytotoxic factor, the method comprising administering to the subject a therapeutically effective amount of an isolated peptide comprising the amino acid sequence FTGN (SEQ ID NO: 1), wherein the combined molecular weight of all amino acids contained within said e tide is lower 2 kDa.

2. The method of claim 1, wherein said peptide is a synthetic peptide.

3. The method of claim 1, wherein said cytotoxic factor is selected from the group consisting of irradiation and chemotherapy.

4. The method of claim 1, comprising administering the isolated peptide to the subject before or after exposure to said cytotoxic factor.

5. The method of claim 1, wherein said administering comprises exposing bone marrow cells to the isolated peptide and transplanting the exposed bone marrow cells into the subject.

6. The method of claim 5, wherein said transplanting is performed before or after exposing the subject to said cytotoxic factor.

7. The method of claim 1, being for improving the probability of survival of said subject.

* * * * *